(12) United States Patent
Kunimoto et al.

(10) Patent No.: US 6,773,565 B2
(45) Date of Patent: Aug. 10, 2004

(54) NOX SENSOR

(75) Inventors: Akira Kunimoto, Kumagaya (JP); Takashi Ono, Kumagaya (JP); Masaharu Hasei, Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 284 days.

(21) Appl. No.: 09/884,340

(22) Filed: Jun. 20, 2001

(65) Prior Publication Data

US 2002/0017461 A1 Feb. 14, 2002

(30) Foreign Application Priority Data

Jun. 22, 2000 (JP) ........................................ 2000/187185
Feb. 19, 2001 (JP) ........................................ 2001/041934

(51) Int. Cl.[7] ........................................... G01N 27/407
(52) U.S. Cl. ...................... 204/425; 204/426; 204/427; 205/781
(58) Field of Search ................................. 204/421–429; 205/781

(56) References Cited

U.S. PATENT DOCUMENTS 4,132,615 A * 1/1979 Linder et al.
6,303,011 B1 * 10/2001 Gao et al.
6,319,377 B1 * 11/2001 Hasei et al.

FOREIGN PATENT DOCUMENTS

| DE | 198 27 927 A1 | 12/1998 |
| DE | 198 52 247 A1 | 6/1999 |
| EP | 0 517 366 A1 | 12/1992 |
| EP | 0 903 575 A1 | 3/1999 |
| JP | 11-23526 A | 1/1999 |
| JP | 11-023526 A | 1/1999 |

* cited by examiner

*Primary Examiner*—Kaj K. Olsen
(74) *Attorney, Agent, or Firm*—Kubovcik & Kubovcik

(57) ABSTRACT

The present invention discloses a NOx sensor for accurately detecting the total concentration of nitrogen oxides in a measured gas without being affected by interference gases. The sensor comprises a gas treatment chamber 5 arranged at the prior stage of the gas detection chamber 3, an inorganic porous member 25 loaded in the gas treatment chamber, and a NOx conversion pumping cell 14, 15 and/or an oxygen supplying pumping cell which supplies oxygen into the gas treatment chamber. When the measured gas is introduced in the gas treatment chamber, the interference gases contained in the measured gas are effectively oxidized by the supplied oxygen under the assistance of the catalytic activity of inorganic porous member. The total amount of the nitrogen oxides is measured in the gas detection chamber while NOx in the measured gas are converted into a single component ($NO_2$ or NO) by the NOx conversion pumping cell after the interference gases are oxidized.

25 Claims, 20 Drawing Sheets

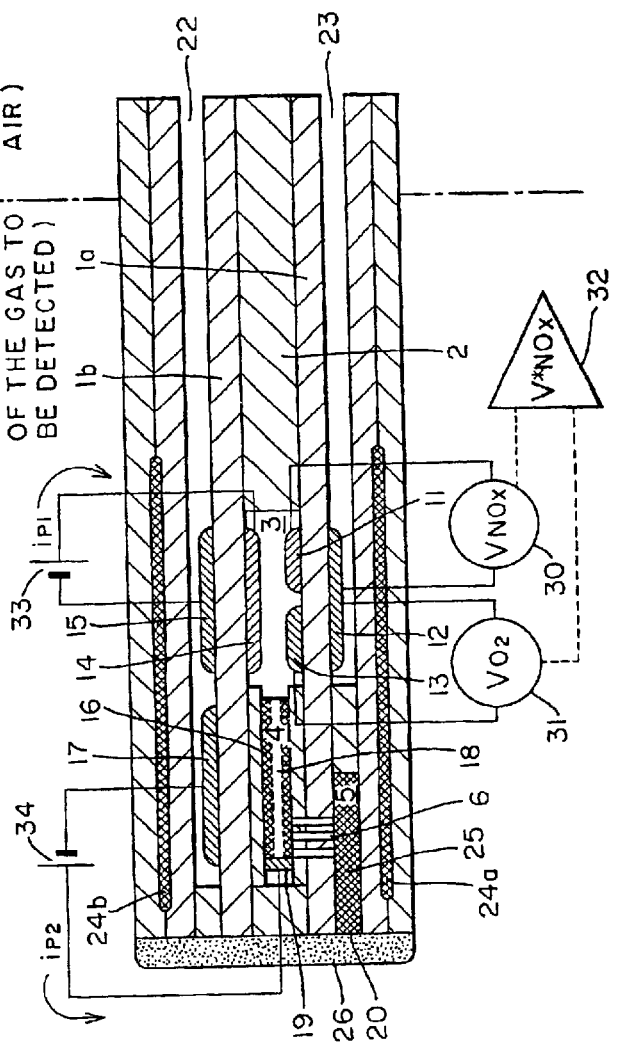
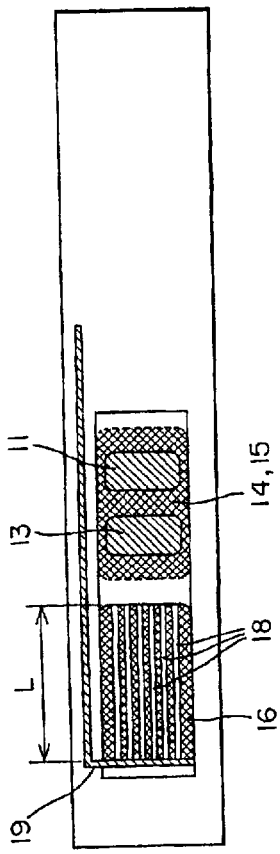
FIG. 13a
FIG. 13b

NOX SENSOR

BACKGROUND OF THE INVENTION

1. Field of the Invention

The present invention relates to a NOx sensor, and more particularly to a NOx sensor for detecting the total concentration of nitrogen oxides in combustion exhaust gases.

2. Description of the Related Art

In recent years much attention has been paid to solid type gas sensors which can be directly inserted into automotive and other engine exhaust gases for continuous measurement. Many reports have been made on the research and development thereof. The present inventors have already proposed mixed potential type NOx sensors which are capable of real-time measurement of the total NOx concentration in exhaust gases. For example, Japanese Patent Laid-Open Publication No. Hei 11-23526 describes a configuration in which a NOx sensing electrode of mixed potential type is installed in a gas detection chamber composed of an internal space formed by zirconia solid electrolytes, and a NOx conversion electrode (oxygen pumping cell) is opposed thereto within the same detection chamber. That is, NOx (NO and $NO_2$) in the exhaust gas is electrochemically converted into simple $NO_2$ gas so that the NOx sensing electrode detects the $NO_2$ concentration as the total NOx concentration.

In the Japanese Patent Laid-Open Publication No. Hei 11-23526, a NOx conversion pumping cell for converting NOx into $N)_2$ in the detection chamber is provided along with the oxygen pumping cell for adjusting the oxygen concentration within the detection chamber. Besides the aforementioned NOx sensing electrode and reference electrode, an oxygen sensing electrode for measuring the oxygen concentration in the chamber is also installed in the detection chamber. In this sensor configuration, the potential of the oxygen sensing electrode resulting from the oxygen concentration in the same atmosphere is used as the reference potential of the NOx sensing electrode so that the output of the NOx sensor is less subject to variations in the oxygen concentration of the gas detection chamber.

Nevertheless, in for example the cases of automotive exhaust gas, there also exists such interference gases as hydrocarbon gas (HC) and CO which tend to affect the detection accuracy of the NOx concentration to be measured. Thus, in order for the conventional sensor device to maintain a higher oxygen concentration in its detection chamber, the oxygen pumping cell has been installed at the prior stage of the NOx detection chamber so that oxygen is supplied into the detection chamber while HC and the like are oxidized and removed on the surface of an oxygen pumping electrode (anode electrode).

In other words, the intention has been that the catalysis of the oxygen pumping electrode installed at the prior stage of the detection chamber and the catalysis of the zirconia solid electrolytes forming the detection chamber oxidize such interference gases as HC and CO which approach the detection chamber. The interference gases are thereby converted into $H_2O$ and $CO_2$ which have no effect on the NOx detection.

In the conventional method, however, if concentrations of the reducing gases or the gases to be oxidized and removed in the gas to be detected are too high, the catalysis-based oxidation and removal described above becomes more difficult. More specifically, HC, CO, and others that are left neither oxidized nor removed come into contact with the NOx sensing electrode at the subsequent stage of the detection chamber, thereby giving an output reverse to the $NO_2$ detection output. Accordingly, there has been a high possibility that the detection of the total NOx concentration might become inaccurate if the reducing gases are thus insufficiently removed.

As described above, in the conventional sensor structure, it has been impossible to oxidize and remove HC and other reducing gases in the gas to be detected sufficiently by simply maintaining a high oxygen concentration in the detection chamber, and utilizing the catalytic activity of the oxygen pumping electrode and the zirconia solid electrolyte and the like. Accordingly, there has been a problem that when the gas to be detected contains high amounts of reducing gases such as HC, the total NOx concentration cannot be measured accurately. Therefore, means has been desired which can measure the total NOx concentration accurately even if high concentrations of reducing gases such as HC and CO coexist.

SUMMARY OF THE INTENTION

In order to achieve the object aforementioned, there is provided a NOx sensor comprising: a gas detection chamber composed of an internal space surrounded by zirconia solid electrolyte substrates having oxygen ion conductivity; a NOx sensing cell including a NOx sensing electrode fixed onto the zirconia solid electrolyte substrate in the gas detection chamber, the NOx sensing electrode being active to NOx and oxygen, and a reference electrode fixed onto the zirconia solid electrolyte substrate, the reference electrode being active to at least oxygen; a NOx conversion pumping cell including a NOx conversion electrode fixed onto the zirconia solid electrolyte substrate in the gas detection chamber, the NOx conversion electrode being active to NOx and oxygen, and a counter electrode to be paired with said NOx conversion electrode, the counter electrode being fixed onto the zirconia solid electrolyte substrate, being active to oxygen; voltage applying means for applying a predetermined voltage to the NOx conversion pumping cell; a first gas treatment chamber communicating with the gas detection chamber and having a gas inlet leading to an atmosphere of a gas to be detected, an inorganic porous member being loaded into the first gas treatment chamber; and means for measuring a potential difference between the NOx sensing electrode and the reference electrode while converting NOx in the gas to be detected into single component after a reducing gas in the gas to be detected is oxidized in the first gas treatment chamber, and thereby detecting a total NOx concentration in the gas to be detected. In the sensor of the present invention, the first gas treatment chamber loaded with the inorganic porous member is arranged at the prior stage of the gas detection chamber. Then, the porous member of the first gas treatment chamber is filled with a high concentration of oxygen to be supplied to the internal space of the device by an oxygen supplying pumping cell or the NOx conversion pumping cell. Reducing gases are therefore oxidized and removed by the catalysis of the porous member.

In a preferred embodiment of the NOx sensor according to the present invention further comprising:

an oxidation catalyst pumping cell including an oxidation catalyst electrode composed of the inorganic porous member loaded into the first gas treatment chamber, the oxidation catalyst electrode serving as an anode electrode, and a cathode electrode to be paired with the oxidation catalyst electrode, the cathode electrode being arranged on a zirconia electrolyte substrate outside the gas detection chamber and being active to oxygen; and voltage applying means for applying a predetermined voltage to the oxidation catalyst pumping cell. In this configuration, the gas to be detected, containing reducing gases, flows into the gas detection chamber while making contact with the oxidation catalyst electrode. Thus, the reducing gases in the gas to be detected are electrochemically oxidized on the oxidation catalyst electrode. That is, the provision of the porous oxidation catalyst electrode active to the reducing gases and the supply of active oxygen to the oxidation catalyst electrode force the reaction to occur on the oxidation catalyst electrode so as to prevent HC from flowing into the gas detection chamber.

In another embodiment of the NOx sensor according to the second aspect of the present invention, at least one narrow path, or a gas diffusion path, is arranged between oxidation catalyst electrodes placed in the first gas treatment chamber. Here, the catalyst electrodes need not be porous, but it is desirable that they are porous in terms of performance. In this configuration, the gas to be detected, containing reducing gases, flows into the gas channel in the oxidation catalyst electrode while supplying the oxidation catalyst electrode with active oxygen using the oxidation catalyst pumping cell so as to effectively oxidize and remove the reducing gases.

BRIEF DESCRIPTION OF THE DRAWINGS

FIG. 13($a$) shows a cross sectional view of another embodiment of the sensor structure according to the first aspect of the present invention, 13($b$) shows a diagram of the over view structure of the detection chamber.

DETAILED DESCRIPTION OF THE PREFERRED EMBODIMENTS

Figure 1:
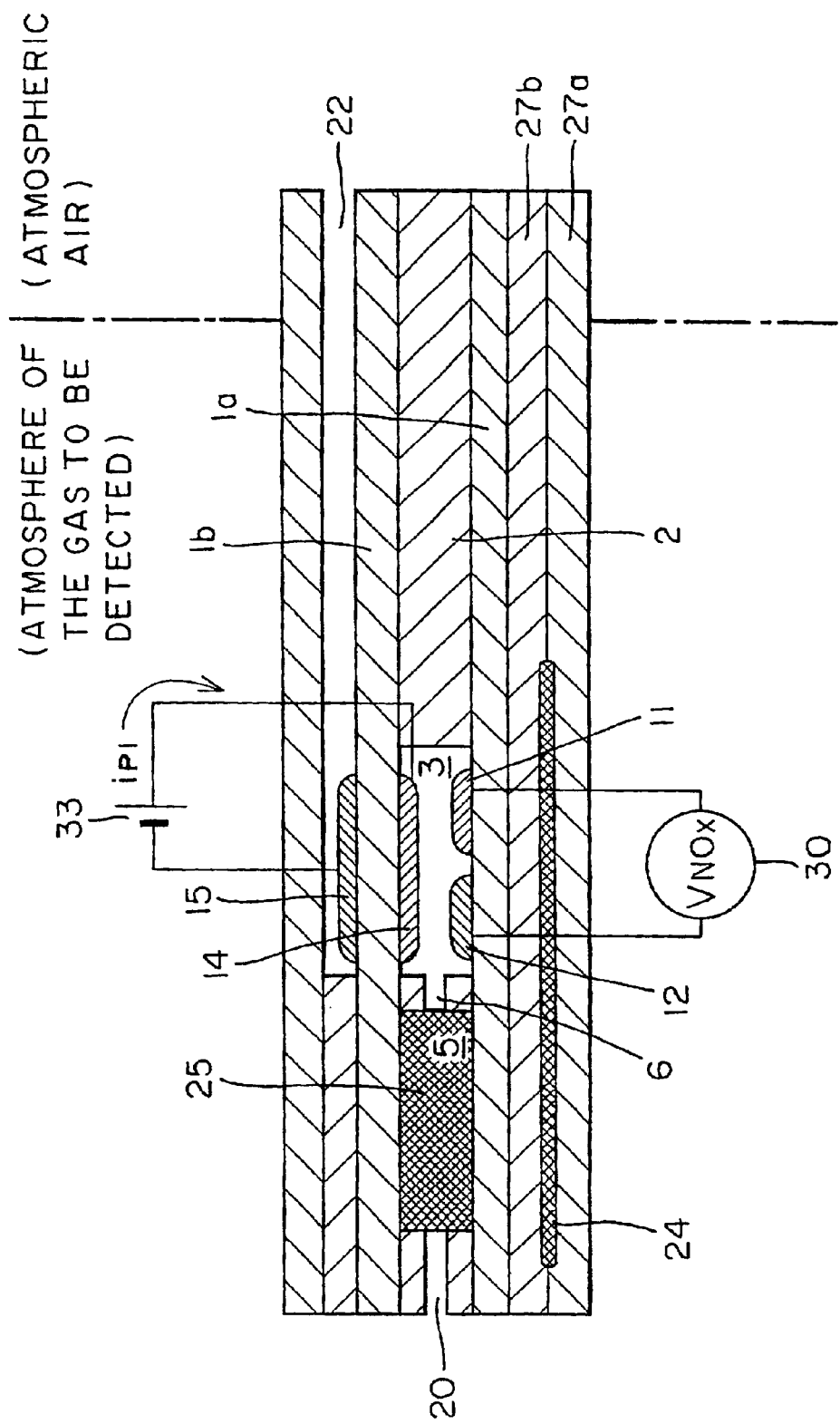
FIG. 1 shows a cross sectional view of an embodiment of the sensor structure according to the first aspect of the present invention.

FIG. 1 shows an embodiment of a sensor device structure which is the most essential for the present invention. In FIG. 1, a NOx sensing electrode 11 is fixed in an internal space (gas detection chamber) 3 which is surrounded by oxygen ion conductors or a first zirconia solid electrolyte substrate 1$a$ and a second zirconia solid electrolyte substrate 1$b$, and a spacer 2. A NOx conversion electrode (anode electrode) 14 constituting a NOx conversion pumping cell is fixed in the gas detection chamber 3 so as to face the NOx sensing electrode 11. A counter electrode to the NOx conversion electrode, or a cathode electrode 15, to be paired with the NOx conversion electrode 14 to form the NOx conversion pumping cell, is fixed in an air introducing duct 22 which leads to the air.

A reference electrode 12 to be paired with the NOx sensing electrode 11 is installed in the same atmosphere as the NOx sensing electrode 11. This structure enables the concentration of NOx to be detected accurately even when the concentration of oxygen in the gas detection chamber varies. The NOx sensing electrode 11 and the reference electrode 12 constitute a NOx detection cell.

Placed at the prior stage of the gas detection chamber 3 is a first gas treatment chamber 5, which is loaded with a porous member 25 composed of an inorganic substance. The porous member may be composed of plural types of inorganic substances. A gas diffusing hole 6 can be arranged between the gas detection chamber 3 and the first gas treatment chamber 5 loaded with the porous member to control the inflow of gas. However, the wall with this gas diffusing hole need not necessarily be installed. That is, the gas inflow control by the gas diffusing hole 6 may be substituted by a porosity adjustment of the porous member 25. Similarly, as shown in FIG. 1, for controlling the gas inflow a gas inlet 20 for introducing a gas to be detected into the first gas treatment chamber 5 may also be adjusted in size while the porous member 25 itself can be adjusted in porosity.

For the sensor structure of FIG. 1 to detect the total concentration of NOx in the gas to be detected, a predetermined D.C. voltage is applied across the anode electrode 14 and the cathode electrode 15 of the NOx conversion pumping cell. The NOx sensing electrode 11 needs to be installed inside the gas detection chamber 3. The NOx sensing electrode 11, in the present invention, uses a mixed potential type sensing electrode. The mixed potential type sensing electrode obtains an electrode potential that is caused by two or more kinds of electrochemical reactions occurring on the electrode.

For example, NO detection involves reactions given by the equations (1) and (2); while $NO_2$ detection involves those given by the equations (3) and (4). In other words, NO detection and $NO_2$ detection are opposite to each other in the direction of reaction, outputting contradictory potentials.

Thus, if NO and $NO_2$ coexist, the outputs cancel each other out, preventing accurate detection of the total NOx concentration.

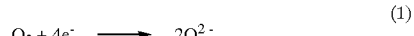
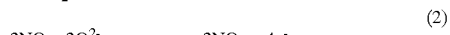
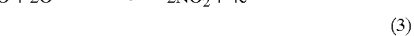
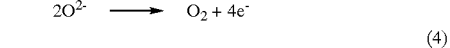

$$O_2 + 4e^- \longrightarrow 2O^{2-} \quad (1)$$
$$2NO + 2O^{2-} \longrightarrow 2NO_2 + 4e^- \quad (2)$$
$$2O^{2-} \longrightarrow O_2 + 4e^- \quad (3)$$
$$2NO_2 + 4e^- \longrightarrow 2NO + 2O^{2-} \quad (4)$$

On that basis, in the sensor structure of FIG. 1 according to the present invention, NO in the gas to be detected is forced by the NOx conversion pumping cell for electrochemical conversion into $NO_2$. Then, the total NOx concentration is detected in terms of the concentration of converted $NO_2$. In a conventional NOx sensor, HC and others left unremoved might flow into the gas detection chamber to be detected as mixed potentials on the NOx sensing electrode. Taking propylene ($C_3H_6$) as an example, the reactions on the electrode at that occasion are given by equations (5) and (6), in the same direction of output as that of NO detection. This shows that the coexistence of HC reduces the output of $NO_2$ detection (total NOx concentration). This also means an unusual output increase for NO detection.

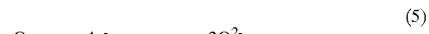
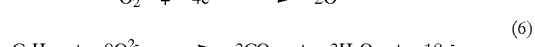

$$O_2 + 4e^- \longrightarrow 2O^{2-} \quad (5)$$
$$C_3H_6 + 9O^{2-} \longrightarrow 3CO_2 + 3H_2O + 18e^- \quad (6)$$

On that basis, in the sensor of the present invention, the first gas treatment chamber loaded with the inorganic porous member 25 is arranged at the prior stage of the gas detection chamber. Then, the porous member of the first gas treatment chamber is filled with a high concentration of oxygen to be supplied to the internal space of the device by an oxygen supplying pumping cell or the NOx conversion pumping cell. Reducing gases are therefore oxidized and removed by the catalysis of the porous member.

The gas detection chamber 3 and the first gas treatment chamber 5 require such a high oxygen concentration so that reducing gases are sufficiently oxidized for removal. For a faster response in gas detection, sensing electrodes of mixed potential type require an oxygen concentration of at least 0.1% by volume. Moreover, in order for the reducing gases in combustion exhaust gas to be sufficiently oxidized and removed in the first gas treatment chamber 5, an oxygen concentration of 1% or higher by volume is necessary. Accordingly, when the porous member loaded into the gas treatment chamber does not constitute an oxidation catalyst pumping cell, the porosity of the porous member 25 is favorably set at 5–40% by volume, and yet preferably at 10–30% by volume. Porosities below 5% by volume reduce the gas diffusion speed to lower the gas response time. At porosities above 40% by volume, the oxygen concentration in the first gas treatment chamber can be no longer maintained sufficiently high, failing to offer an appropriate reducing gas throughout.

Here, the porous member to be loaded into the first gas treatment chamber is made of a substance that comprises mainly at least one among zeolite, zirconia, alumina, and silica, and/or a compound thereof. Porous members composed of alumina-silica mixtures and/or compounds may also be used. In this case, the materials of the porous members themselves are high in catalytic activity and easier to adjust in porosity. Instead of charging these porous members into the first gas treatment chamber, powdered material of the above-mentioned porous members may be loaded. In this case, it is preferable that an additional porous film comprising an inorganic substance is formed at the front of the gas inlet.

The porous member 25 may carry a catalyst for promoting the oxidation of the reducing gases. In this case, it is preferable to use one or more of the catalytic precious metals, Pt, Pd, Ir, Au, Ru, Ag, and Rh. Besides, high catalytic activity can be obtained by adding a catalytic precious metal of 0.1–30 mg/cm$^3$ with respect to the bulk volume of the porous member. If this carried amount falls below 0.1 mg/cm$^3$, effect of the catalysis is too small. Conversely, the catalytic activity decreases if the amount exceeds 30 mg/cm$^3$. The carried amount of the catalyst preferably ranges from 0.5 to 10 mg/cm$^3$.

Among these precious metal catalysts, Rh carried as the catalyst in particular can exert high catalysis as long as water vapor lies in the atmosphere around the catalyst even under extremely low oxygen concentration or in a situation of absolutely no oxygen. That is, in view of the use in combustion exhaust gas, the sensor detectability can be maintained even in the high reductive atmosphere. Moreover, carrying both Rh and Pt allows an improvement in catalytic power. Besides, when Rh is used as a catalyst, a carrier comprising mainly zirconia or a carrier made of zeolite can be used for a further improvement in performance. The carrier employed herein substantially refers to the aforementioned inorganic porous member or powder.

The catalyst carried by the porous member may be oxides. In this case, high-catalytic ceria or a solid solution of ceria and zirconia is used effectively. The ceria-zirconia solid solution can also be used to adsorb oxygen. The oxygen adsorbed in this solid solution can be utilized to maintain the oxygen catalysis of the porous member even at the front of the gas inlet where the oxygen supplied from the oxygen supplying pumping cell becomes low in concentration. Therefore, the sensor detectability can be maintained even if the atmosphere is of highly reductive. The ceria-zirconia solid solution preferably contains zirconia of 30–70 mol %. Zirconia compositions below 30 mol % cause greater deterioration in catalytic power, while those above 70 mol % lead to insufficient oxygen adsorption power. A range of 40 and 60 mol % is favorable in terms of sensor performances.

In addition, the aforementioned precious metals can be carried by the catalytic oxides for yet greater improved catalytic performance. Here, the precious metals are also preferably carried in amounts of 0.1–30 mg/cm$^3$ with respect to the bulk volume of the porous member. The carried amounts below 0.1 mg/cm$^3$ provide no effect. Above 30 mg/cm$^3$, the effect reaches saturation and the cost of the precious metal becomes a problem.

Under normal circumstances, the gas sensor of the present invention is heated for use to a high temperature above 300–400° C. Therefore, in the example of FIG. 1, the NOx sensing cell and the NOx conversion pumping cell are directly heated and controlled to a predetermined temperature by an embedded heater 24. Though not shown in the diagram, a thermocouple or the like for detecting the device temperature is arranged in the vicinity of the NOx sensing electrode 11, so that a heater voltage is driven with the device temperature fed back for control. Heater substrates 27a and 27b should be composed of insulators so as to prevent a heater voltage leak. In the case of the device shown in FIG. 1, however, the heater substrates 27a and 27b are integrated with the solid electrolytes. The heater substrates also preferably use solid electrolyte substrates while alumina or other insulative layers are formed between the heater 24 and the heater substrates 27a, 27b. The reason is to prevent substrate exfoliation and cracks due to differences in sintering shrinkage or differences in thermal expansion with respect to the heater substrates when integral sintering is performed on green sheets. Because of the same reason, the spacer 2 described above is also preferably formed of the same solid electrolyte material.

Moreover, in FIG. 1, the first gas treatment chamber loaded with the porous member 25 of the present invention is also exposed to high temperature for effective oxidation and removal of reducing gases. The oxidation and removal of the reducing gases requires that the amount of oxygen pumped by the NOx conversion pumping cell 14, 15 be optimized so that the oxidation functions sufficiently even if the gas to be detected contains no oxygen at all. A predetermined voltage is applied to the NOx conversion pumping cell so that the oxygen necessary for the oxidation and removal of reducing gases in the porous member 25 is introduced into the gas detection chamber 3 through the duct 22 which leads to the air. Specifically, an external power supply (D.C. power supply) 33 is applied across the NOx conversion pumping cell with the conversion counter electrode 15 as the cathode electrode and the NOx conversion electrode 14 as the anode electrode. The predetermined voltage employed herein is not limited to a voltage that is applied constantly. In other words, it includes pumping cell electrodes that are applied in a controlled way to exert a predetermined function.

Meanwhile, for the output of the NOx sensing, a difference in electrode potential between the NOx sensing electrode 11 and the reference electrode 12 is measured. Due to the reason stated before, a potential difference arises between the NOx sensing electrode 11 and the reference electrode 12 when the reference electrode 12 has no electro chemical reaction with the NOx. Therefore, the reference electrode is either composed of NOx-inactive electrode material or configured so as not to be exposed to NOx. When it is inactive to NOx and active to oxygen, the reference electrode 12 can be installed in the same atmosphere as the NOx sensing electrode 11, or inside the gas detection chamber 3 as shown in FIG. 1. According to such a structure, even if the oxygen concentration in the gas detection chamber 3 varies, the NOx sensing electrode 11 and the reference electrode 12 can be rendered equal in oxygen activity to make a significant reduction in the dependency of the sensor output on oxygen concentration. Needless to say, this sensor structure cannot be obtained from other detection schemes of the concentration-cell electromotive force type.

A potentiometer 30 for measuring the potential difference between the NOx sensing electrode 11 and the reference electrode 12 is arranged between the electrodes. While the potentiometer 30 is used as the means for measuring the potential difference between the NOx sensing electrode 11 and the reference electrode 12, the means of measurement is not limited to potentiometers. For example, an additional comparison cell (battery) is connected in parallel to the sensing cell of FIG. 1 to measure a voltage of the comparison cell at which the current flowing through the two cells becomes zero. In this method, the sensor electromotive force can be measured without taking any current out of the sensing cell.

Figure 2:
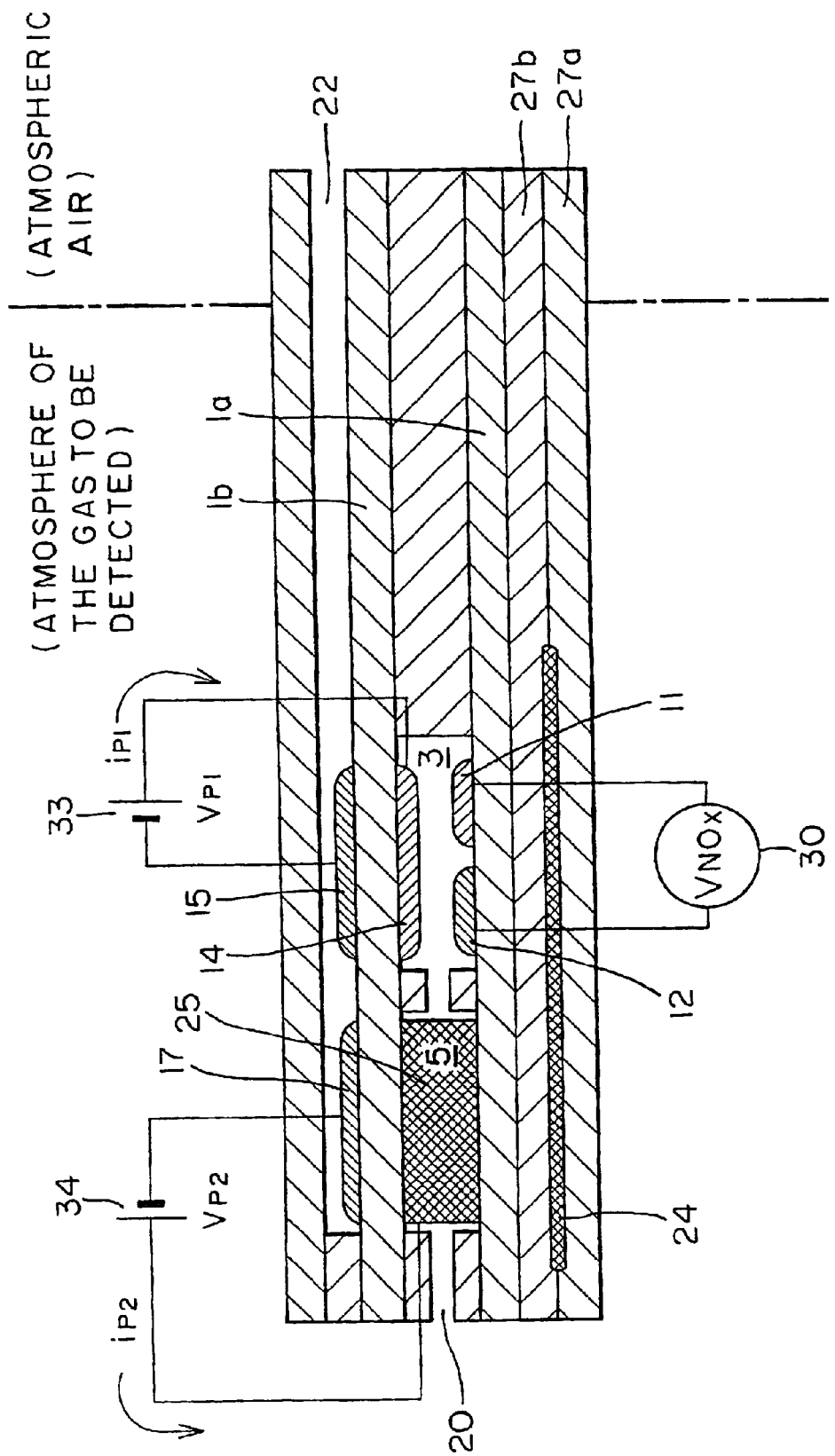
FIG. 2 shows a cross sectional view of another embodiment of the sensor structure according to the first aspect of the present invention.

In FIG. 2, an oxidation catalyst pumping cell is made up using the inorganic porous member 25 loaded into the first gas treatment chamber 5 as an oxidation catalyst electrode (anode electrode). Here, a cathode electrode 17 to be paired with the oxidation catalyst electrode is installed on the zirconia solid electrolyte outside the gas detection chamber. Voltage applying means 34 is provided to apply a predetermined voltage to the oxidation catalyst pumping cell. In this configuration, the gas to be detected, containing reducing gases, flows into the gas detection chamber 3 while making contact with the oxidation catalyst electrode 25. Thus, the reducing gases in the gas to be detected are electrochemically oxidized on the oxidation catalyst electrode. That is, the provision of the porous oxidation catalyst electrode active to the reducing gases and the supply of active oxygen to the oxidation catalyst electrode force the reaction (6) to occur on the oxidation catalyst electrode so as to prevent HC from flowing into the gas detection chamber. The voltage applied across the oxidation catalyst pumping cell is set to a range where the electrochemical oxidation current is effectively obtained.

Figure 4:
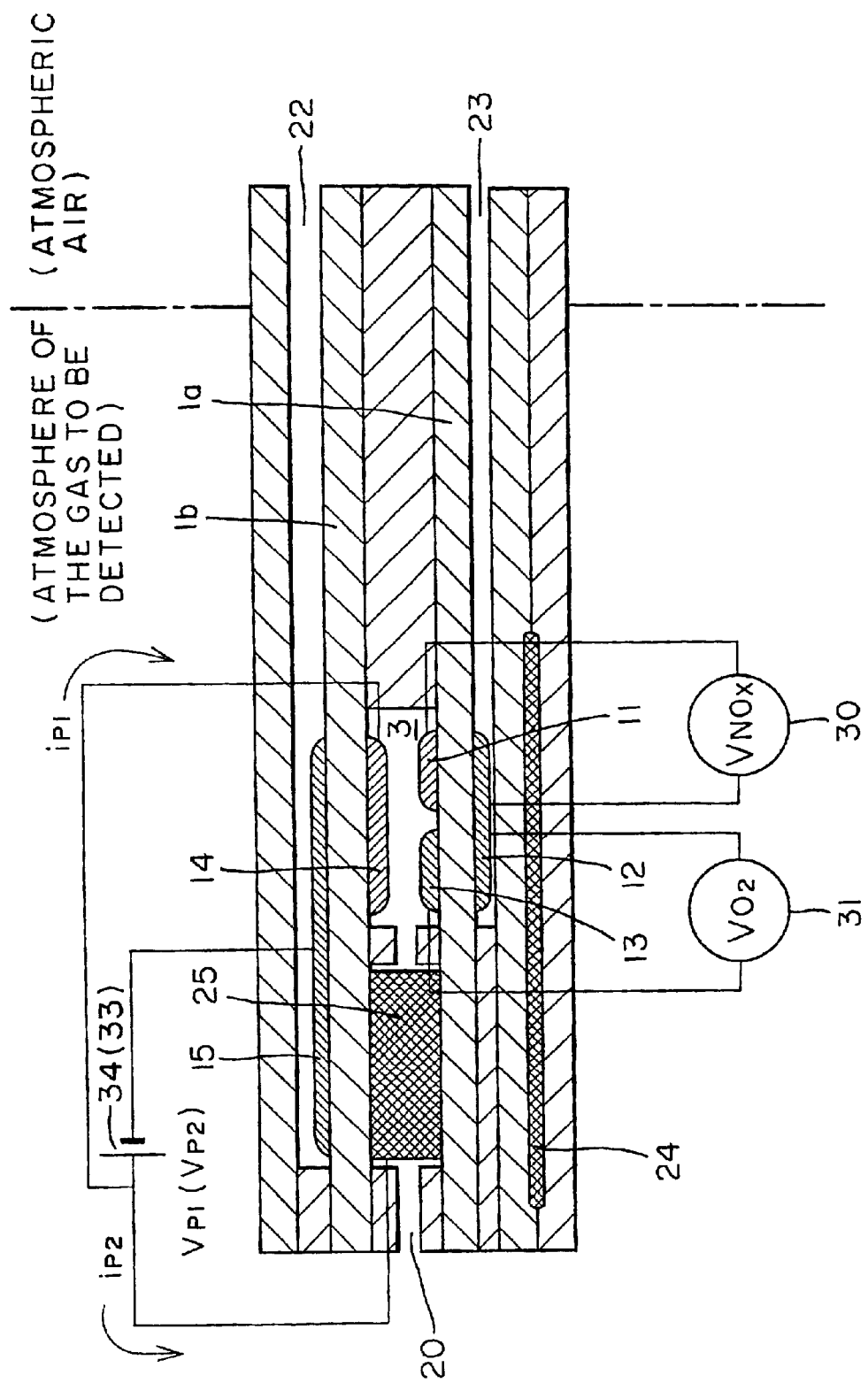
FIG. 4 shows a cross sectional view of another embodiment of the sensor structure according to the first aspect of the present invention.

In FIG. 2, the NOx convertion pumping cell is composed of the NOx conversion electrode 14 as anode electrode and the counter electrode 15 to be paired with the NOx conversion electrode as cathode electrode. Here, a predetermined voltage is applied to the NOx conversion pumping cell as to convert NO in the gas to be detected into $NO_2$. When oxidation catalyst pumping cell or oxygen supplying pumping cell is installed in the sensor structure and supplies oxygen into the gas treatment chamber, the current of the NOx conversion pumping cell can be changed in the opposite direction because the reduction gas (contained in the gas to be detected) is oxidized. That is, the NOx convertion pumping cell could be composed of the NOx conversion electrode 14 as cathode electrode and the counter electrode 15 to be paired with the NOx conversion electrode as anode electrode. In this case, $NO_2$ in the gas to be detected is forced to convert into NO, and the total NOx concentration is detected in terms of the concentration of NO. In the sensor structure shown in FIG. 2, the counter electrodes (cathode electrodes) 15 and 17 of the NOx conversion pumping cell and the oxidation catalyst pumping cell are separately installed in the air introducing duct 22. However, as shown in FIG. 4, they maybe formed as a single electrode.

In the present structural example, at least the substrates on which the sensing cell (reference electrode), the oxidation catalyst pumping cell, and the NOx conversion pumping cell are formed must be a solid electrolyte of an oxygen ion conductor. Regarding a suppression strain in the sensor body, caused by the sintering process during fabrication, all substrates are preferably made of the same solid electrolyte.

Figure 3:
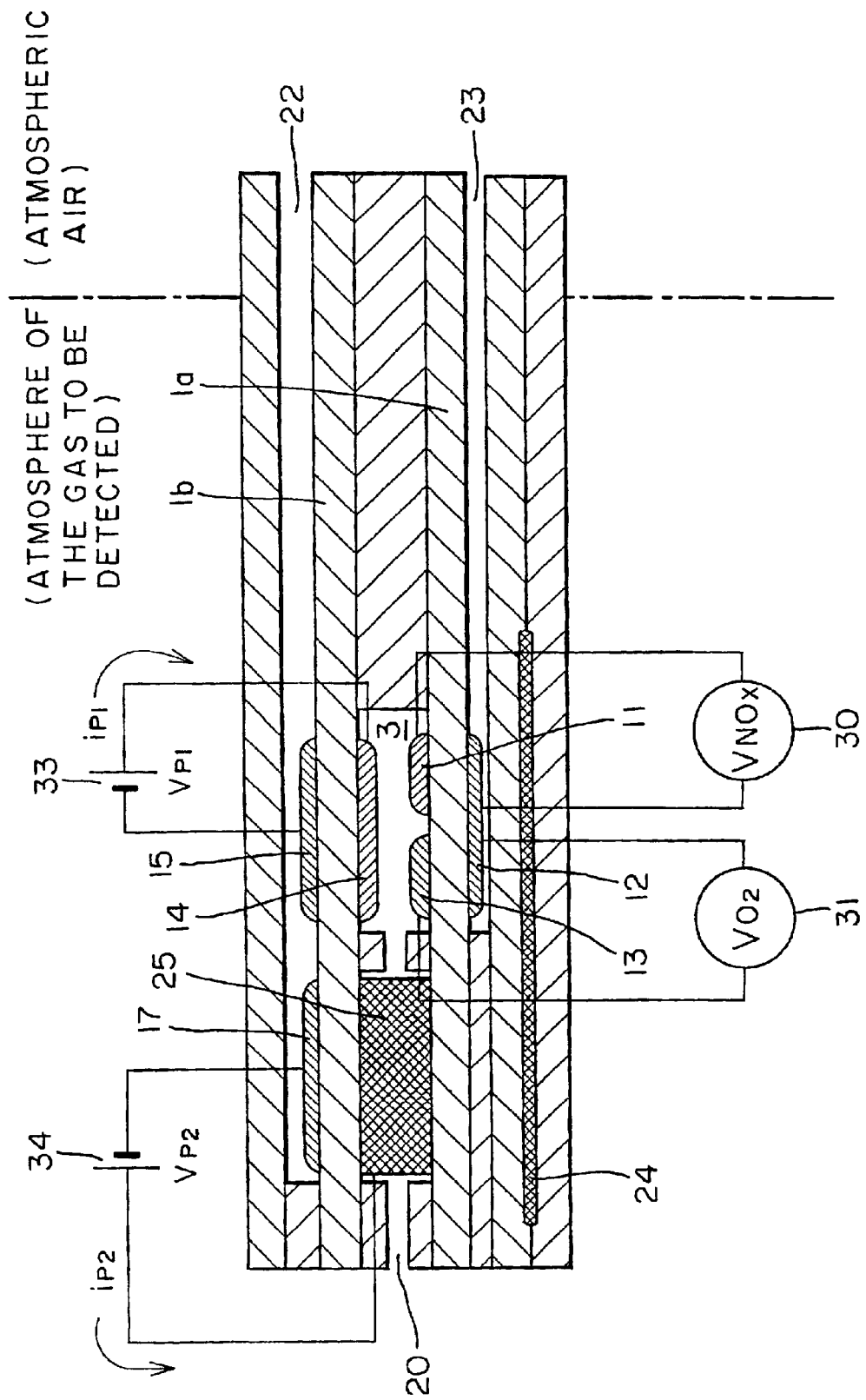
FIG. 3 shows a cross sectional view of another embodiment of the sensor structure according to the first aspect of the present invention.

Now, as shown in FIG. 3, an $O_2$ sensing electrode 13 is arranged in the gas detection chamber 3. Here, for output correction the potential difference from the reference electrode 12 arranged in an air reference duct is combined with a potential difference similarly obtained between the NOx sensing electrode 11 and the reference electrode 12. This allows an improvement in the detecting accuracy of the sensor. More specifically, although the NOx sensing electrode and the $O_2$ sensing electrode have some difference in their dependency on the partial pressure of oxygen, an appropriate factor can be provided to the detecting circuit so that the dependency is eliminated even if the atmosphere of the gas to be detected varies greatly in oxygen concentration. In addition, the output from between the $O_2$ sensing electrode and the reference electrode can also be used to measure directly the partial pressure of oxygen in the gas detection chamber 3 and control the driving voltage of an additional oxygen pumping cell (not shown) to achieve oxygen concentration control in the gas detection chamber.

The gas to be detected diffuses into the gas detection chamber 3 through the gas inlet 20. For example, in the case of detecting the concentration of NOx in the combustion exhaust gas of an automobile or the like, the NOx includes both NO and $NO_2$. Also, there exist other gases including hydrocarbon gas (HC), CO, $CO_2$, and $H_2O$. In order to detect the total concentration of NOx therein, it is necessary to remove the other gases which affect the sensor output and to convert $NO_2$ or NO into a single gas. On that basis, the oxidation catalyst electrode 25 forcefully oxidizes HC and other reducing gases with active oxygen, and the NOx conversion electrode 14 converts $NO_2$ into the single gas as described above. To use such a gas conversion treatment mechanism for detection of the total NOx concentration, the oxygen concentration in the gas detection chamber 3 must be set at 1% or higher by volume.

In the cases of exhaust gases from automotive gasoline engines and the like, however, HC, CO, and other reducing gases therein need to be removed even in regions short of combustion air (fuel rich regions). This requires that the oxidation catalyst electrode 25 installed in the first gas treatment chamber 5 be capable of oxidizing HC and the like even without oxygen in the atmosphere. In other words, simply having an oxidation and removal capability with catalytic activity might, for example, fail to oxidize or remove reducing gases in the aforesaid fuel rich atmosphere. According to the oxidation catalyst electrode of the present invention, active oxygen is continuously supplied onto the oxidation catalyst electrode. Therefore, even in an atmosphere without oxygen, the gas to be detected can be passed through the oxidation catalyst electrode for reducing-gas oxidation and removal.

Figure 5:
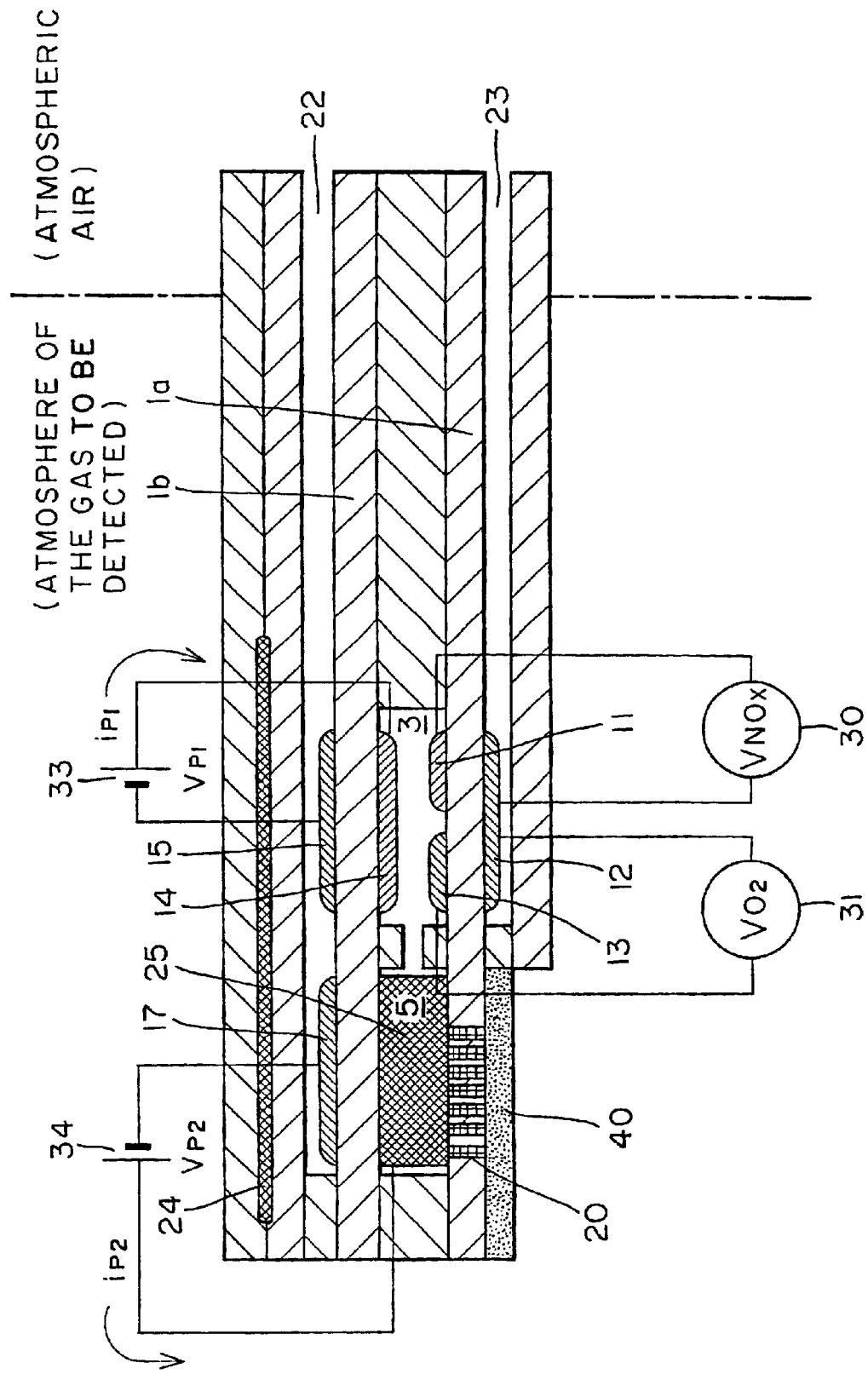
FIG. 5 shows a cross sectional view of another embodiment of the sensor structure according to the first aspect of the present invention.

FIG. 5 shows one in which gas inlets 20 leading to the first gas treatment chamber are formed in the bottom of the first gas treatment chamber 5. In FIG. 5, plural of through holes are formed as the gas inlets in the zirconia solid electrolyte substrate 1a. However, these through holes are not specially restrictive. Namely, a porous substrate or thick film equivalent to gas inlets maybe used. Besides, a protective layer 40 is preferably formed over the gas inlets 20. Needless to say, this protective layer is made of a porous film and not necessarily of solid electrolyte. The use of the present sensor structure allows a reduction in the gas diffusion resistance at the gas inlet(s). This lowers the gas diffusion resistance which is increased by the installation of the oxidation catalyst electrode in the present invention. In other words, while too high a gas diffusion resistance results in longer gas response time, the adoption of the gas introducing method of the present structure can improve the gas response greatly.

Figure 6:
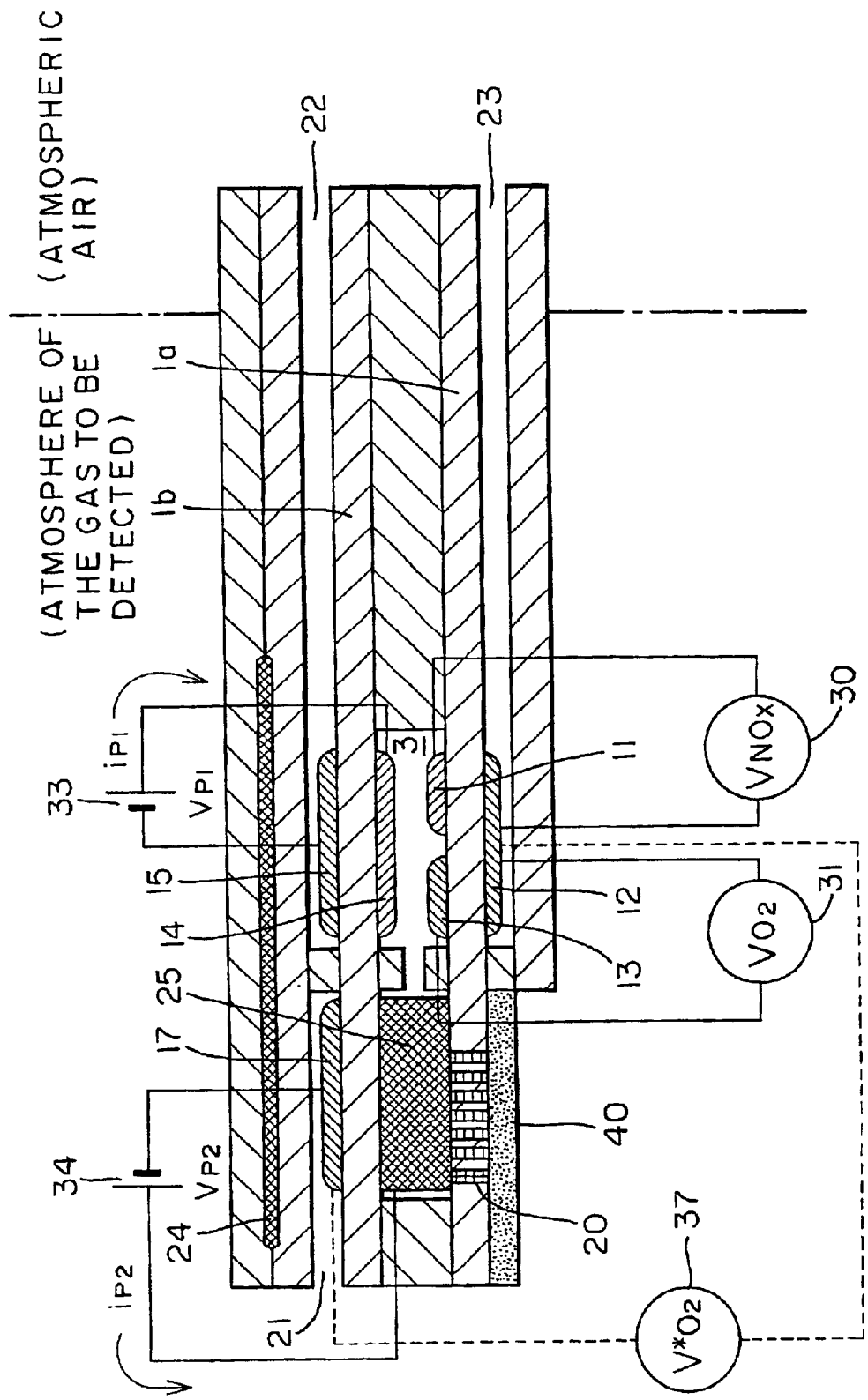
FIG. 6 shows a cross sectional view of another embodiment of the sensor structure according to the first aspect of the present invention.

FIG. 6 shows a structure in which the counter electrode (cathode electrode) 17 of the oxidation catalyst electrode is arranged in a duct 21 which leads to the atmosphere of the gas to be detected. This sensor decomposes $H_2O$ and $CO_2$ in the exhaust gas electrochemically, and uses oxygen ions produced thereby to supply active oxygen to the oxidation catalyst electrode. In this scheme, it is possible to keep supplying the oxidation catalyst electrode with oxygen steadily even if no oxygen exists in the atmosphere of the gas to be detected.

Besides, according to the structure of FIG. 6, the cathode electrode 17 of the oxidation catalyst pumping cell also works as the oxygen sensing electrode which is detecting the oxygen concentration in the measured gas (the gas to be detected). That is, the oxygen concentration in the measured gas could be simultaneously detected from the potential difference $V^*O_2$ between the cathode electrode 17 and the reference electrode 12 fixed in the air atmosphere. Here, gas inlets 20 should be formed through the first zirconia solid electrolyte substrate 1a so that oxygen ion could move in the zirconia solid electrolyte between the cathode electrode 17 and the reference electrode 12. In the structure of FIG. 6, the reference electrode 12 is used as the counter electrode paired with the oxygen sensing electrode detecting the oxygen concentration in the measured gas. The counter electrode 15 to the NOx conversion electrode fixed in the air atmosphere may be also used as that electrode.

Here, gas inlets 20 leading to the first gas treatment chamber are formed in the bottom of the first gas treatment chamber 5. They can be formed in the top of the first treatment chamber 5.

For favorable performance, the oxidation catalyst electrode in the present invention may be formed of any one, mixture or alloy of Pt, Pd, Ir, Au, and Rh, which are particularly active to HC. Moreover, a method of distributing and adding solid electrolytes is employed with the aim of increasing active sites (three-phase interfaces with solid electrolytes) and forming a porous structure. In particular, for the formation of porous structures, for example, powdered solid electrolyte of zirconia may be temporarily fired at low temperature, crushed, and subjected to a particle size adjustment before the addition to the electrode paste. In the method of charging the first gas treatment chamber with the oxidation catalyst electrode, the porosity is set at 10–50% by volume, and preferably 20–40% by volume, for favorable performance. Porosities below 10% by volume decline the gas response property, while those above 50% by volume lower the oxidation removal efficiency. For appropriate porosity and oxidation removal performance, the solid electrolyte of 10–40% by volume is well distributed and added into the oxidation catalyst electrode. Addition of solid electrolyte below 10% by volume hardly increase the three-phase interfaces. In contrast, at addition of solid electrolyte above 40% by volume, the oxidation catalyst electrode drops in electric conductivity. As employed herein, the drop in electric conductivity refers to a state where Pt or other catalyst particles constituting the oxidation catalyst electrode are isolated electrically. This precludes electrochemical actions to decrease the oxidation removal efficiency.

Moreover, the oxidation catalyst electrode may be made of metal oxides that are active to reducing gases. Examples of the metal oxides include NiO, $Cr_2O_3$, $WO_3$, $NiCr_2O_4$, $Ir_2O_3$, PdO, and $RhO_2$. These metal oxides typically have lower electric conductivities. Accordingly, these metal oxides can be added to the aforementioned Pt, Pd, Ir, Au, Rh, and alloys thereof for greater pump currents. Alternatively, metal electrodes thereof and metal oxide electrodes may be laminated.

Figure 7:
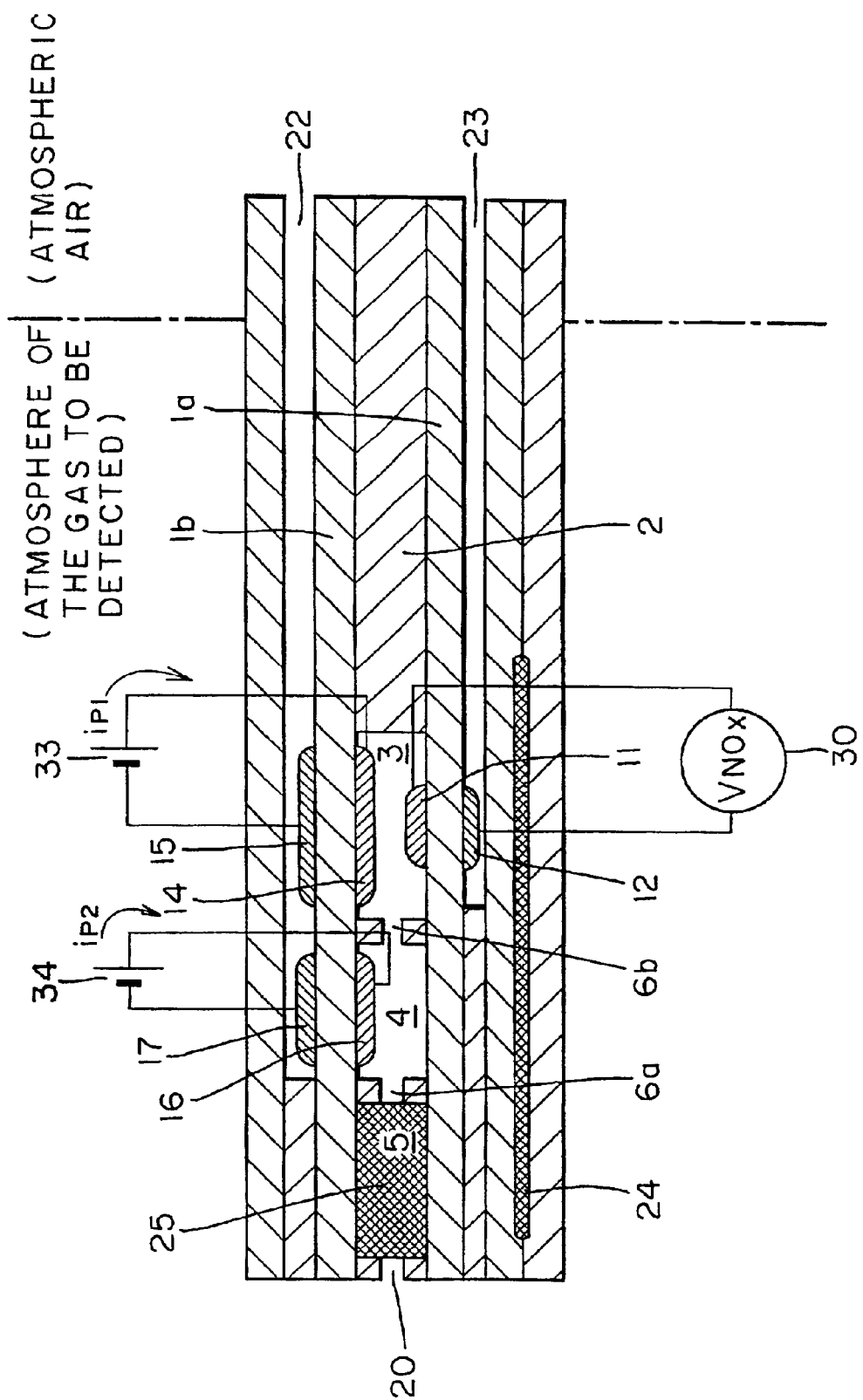
FIG. 7 shows a cross sectional view of another embodiment of the sensor structure according to the first aspect of the present invention.

FIG. 7 shows an embodiment where a second gas treatment chamber 4 is provided between the gas detection chamber 3 and the first gas treatment chamber 5. An oxygen supplying pumping cell for introducing oxygen in the air into the first gas treatment chamber through the air introducing duct 22 is fixed to the solid electrolyte substrate 1b. The oxygen supplying pumping cell is composed of an anode electrode 16 and a cathode electrode 17. An external power supply 34 for driving this oxygen supplying pumping cell 16, 17 is connected to the electrodes. In the example shown in FIG. 7, gas diffusion holes 6a and 6b for limiting gas flow are arranged between the second gas treatment chamber 4 and the first gas treatment chamber 5, and between the second gas treatment chamber 4 and the gas detection chamber 3 respectively.

Due to the reason stated above, the diffusion hole 6a can be omitted. The diffusion hole 6b can also be omitted if the oxygen supplying pumping cell 16, 17 pumps a sufficient amount of oxygen. Now, the reference electrode 12 of the NOx sensing cell 11, 12 is installed in a reference duct 23 which leads to the air. In this case, the reference electrode 12 can be active to oxygen only, which means a wider selection of materials for the reference electrode 12.

Figure 8:
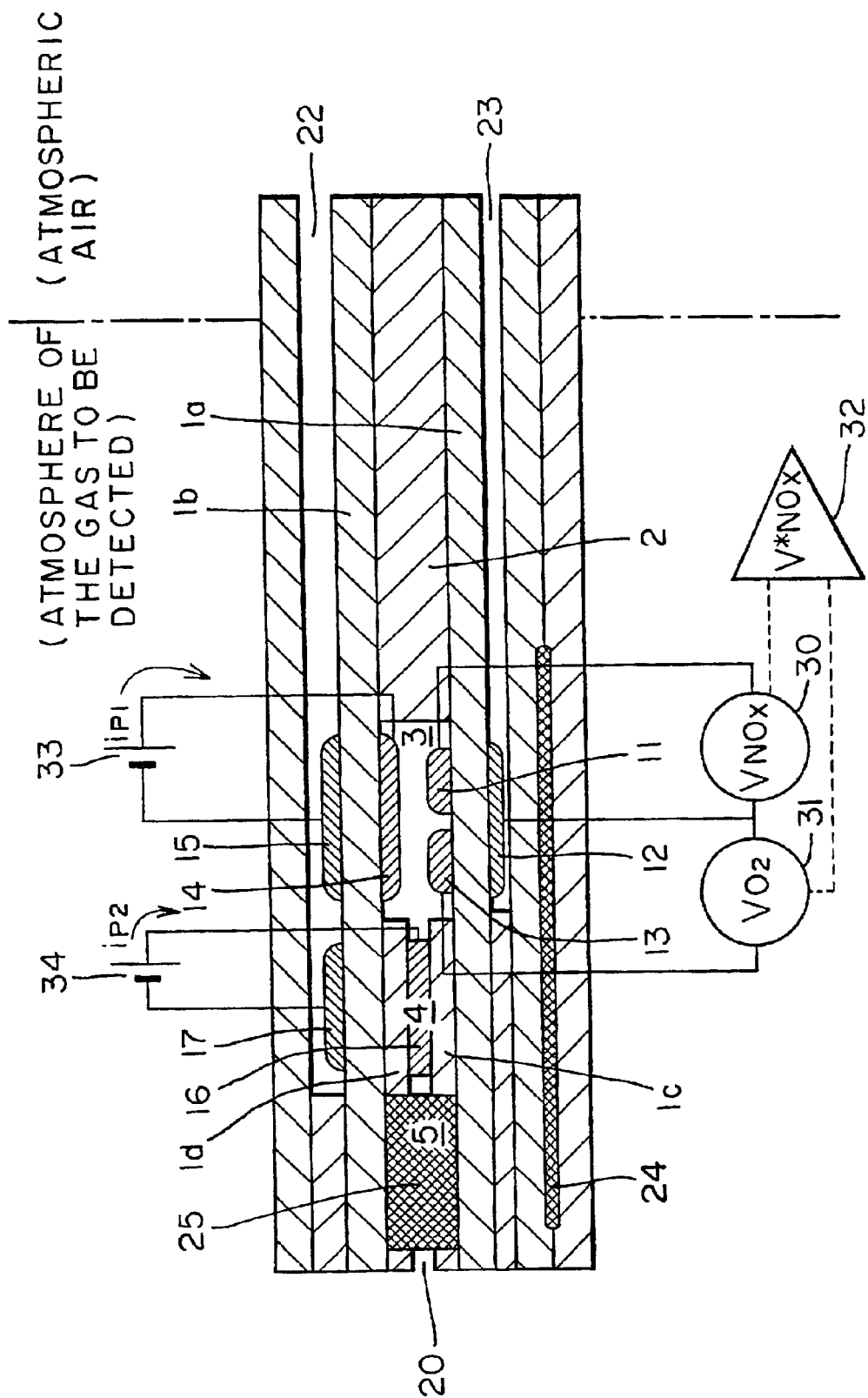
FIG. 8 shows a cross sectional view of another embodiment of the sensor structure according to the first aspect of the present invention.

FIG. 8 shows an embodiment where the anode electrode 16 of the oxygen supplying pumping cell is loaded into the second gas treatment chamber 4. In this case, the gas to be detected flows through the first gas treatment chamber 5 and diffuses into the second gas treatment chamber 4. Here, the gas to be detected passes through the anode electrode 16 of the oxygen supplying pumping cell. This requires that the anode electrode 16 of the oxygen supplying pumping cell be a porous electrode. The anode electrode, or porous electrode, 16 has the desirable twofold function of catalytic oxidation of the reducing gases included in the gas to be detected and electrochemical oxidation thereof under a voltage applied to the oxygen supplying pumping cell. In other words, it is desirable that the anode electrode 16 comprises an oxidation catalytic electrode, active to gases of HC and CO to be treated, and has oxidation catalytic characteristics. It preferably uses a material having the same properties, composition, and porosity as those of the oxidation catalytic electrode loaded into the first gas treatment chamber described above. When the electrochemical activity of the electrode is high, the capacity of the electrochemical treatment can be greatly improved. Now we call the pumping cell 16, 17 as the oxidation catalyst pumping cell, when the anode electrode is set to be active to reducing gases. The voltage applied across the oxidation catalyst pumping cell 16, 17 is set to a range where an effective electrochemical oxidation current is obtained.

Moreover, in FIG. 8, the $O_2$ sensing electrode 13 is also arranged in the gas detection chamber 3 while a reference electrode 12 to be shared with the NOx sensing electrode 11 is installed in the reference duct 23. A potentiometer 30 is connected between the NOx sensing electrode 11 and the reference electrode 12 as means for measuring the potential difference VNOx between them. In addition, a potentiometer 31 is similarly connected between the $O_2$ sensing electrode 13 and the reference electrode 12, as means for measuring the potential difference $VO_2$ between these electrodes.

Furthermore, arithmetic processing means 32 is provided to correct the signals from these potentiometers for variation in oxygen concentration.

The potential difference $VO_2$ is a signal based on the oxygen concentration in the gas detection chamber 3. Arithmetic operations on the potential differences $VO_2$ and VNOx allow an improvement in the detecting accuracy of the NOx concentration. More specifically, although the NOx sensing electrode and the $O_2$ sensing electrode have some difference in the dependency on the partial pressure of oxygen, an appropriate factor can be provided to the detecting circuit which negates the influence thereof even if the atmosphere of the gas to be detected varies greatly in oxygen concentration. The arithmetic processing means 32 is realized with hardware using an electronic circuit, or software using a microcomputer etc. Thereby, the NOx detection can be performed with accuracy even in the cases where variations in the oxygen concentration of the gas atmosphere to be detected affect variations in the oxygen concentration inside the gas detection chamber.

Figure 9:
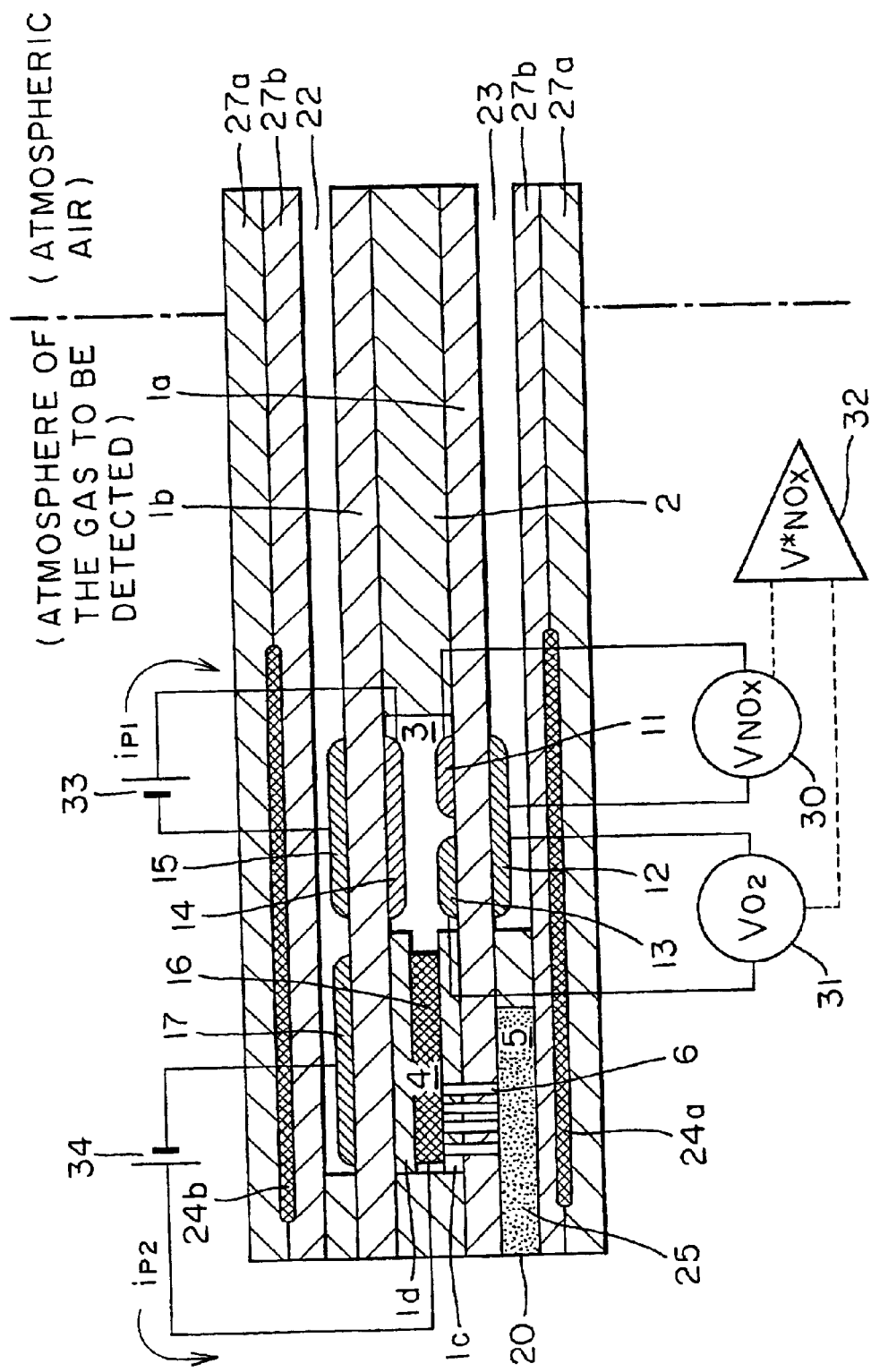
FIG. 9 shows a cross sectional view of another embodiment of the sensor structure according to the first aspect of the present invention.

FIG. 9 shows a structure in which the first gas treatment chamber 5 is formed across the solid electrolyte substrate 1a in a layer different from that of the second gas treatment chamber 4 and the gas detection chamber 3. In this structural example, a plural gas diffusion holes 6 are formed between the first gas treatment chamber 5 and the second gas treatment chamber 4. There is no particular constraint to the number of holes. Instead of the diffusion hole structure shown in the figure, a porous member may be used in place of the gas diffusion holes.

When the gas treatment chambers are separately layered across the solid electrolyte substrate 1a as in the present structural example, it is easy to increase the thicknesses of the layered substrates. Thus, for uniform heating to the device, heaters 24a and 24b are preferably arranged at both sides of the device as shown in the figure. The separate-layered structure of the first gas treatment chamber as shown in FIG. 9 allows the first gas treatment chamber to be effectively filled with the oxygen that is supplied by oxygen pumping cell. Besides, in such a sensor device structure, the first gas treatment chamber can be arranged near the heaters and thereby kept at a higher temperature. This allows more efficient oxidation and removal of the reducing gases in the gas to be detected.

In FIG. 9, the second gas treatment chamber 4 and the gas detection chamber 3 are formed as chambers separated by a wall having gas diffusion holes. Nevertheless, even in structures where the two chambers are turned into a single chamber with no diaphragm, or where the oxygen supplying pumping cell is omitted and the oxygen pumping is performed by the NOx conversion pumping cell alone, the same effect can also be obtained from the separation of the first gas treatment chamber.

Figure 10:
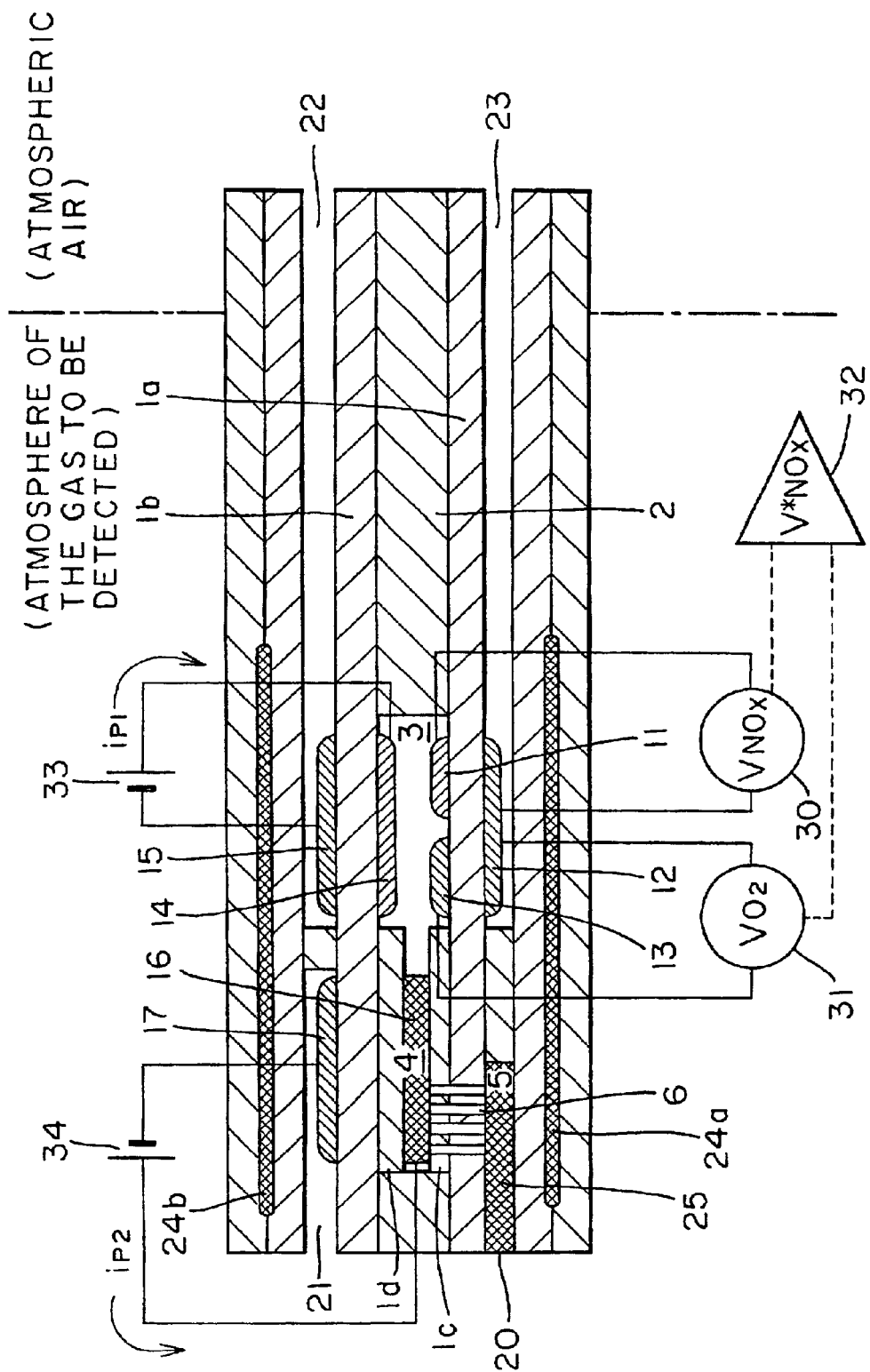
FIG. 10 shows a cross sectional view of another embodiment of the sensor structure according to the first aspect of the present invention.

FIG. 10 shows a structure in which the cathode electrode 17 of the oxygen supplying pumping cell 16, 17 is directly exposed to the atmosphere of the gas to be detected. As has been described, when oxygen-containing compound gases such as $H_2O$ and $CO_2$ exist in the atmosphere of the gas to be detected, for example combustion exhaust gas, the cathode electrodes 15 and 17 of the individual pumping cells can be arranged directly open to the atmosphere of the gas to be detected so that $H_2O$ and $CO_2$ are decomposed electrochemically for oxygen pumping. In particular, in the case of supplying a large amount of oxygen by oxygen pumping cells, it is preferable that at least the oxygen supplied by the oxygen supplying pumping cell is made from the atmosphere of the gas to be detected.

Figure 11:
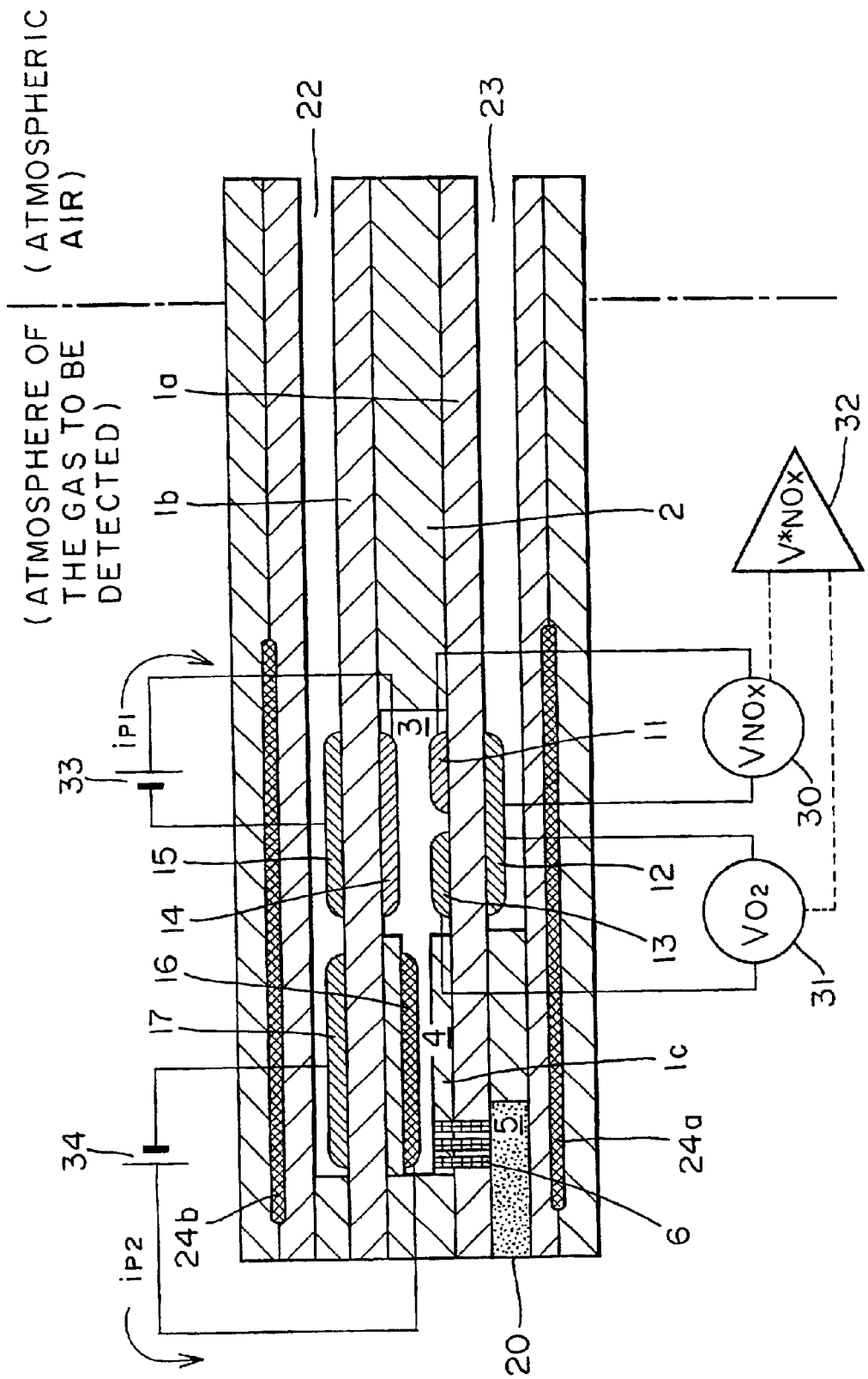
FIG. 11 shows a cross sectional view of another embodiment of the sensor structure according to the first aspect of the present invention.
Figure 12:
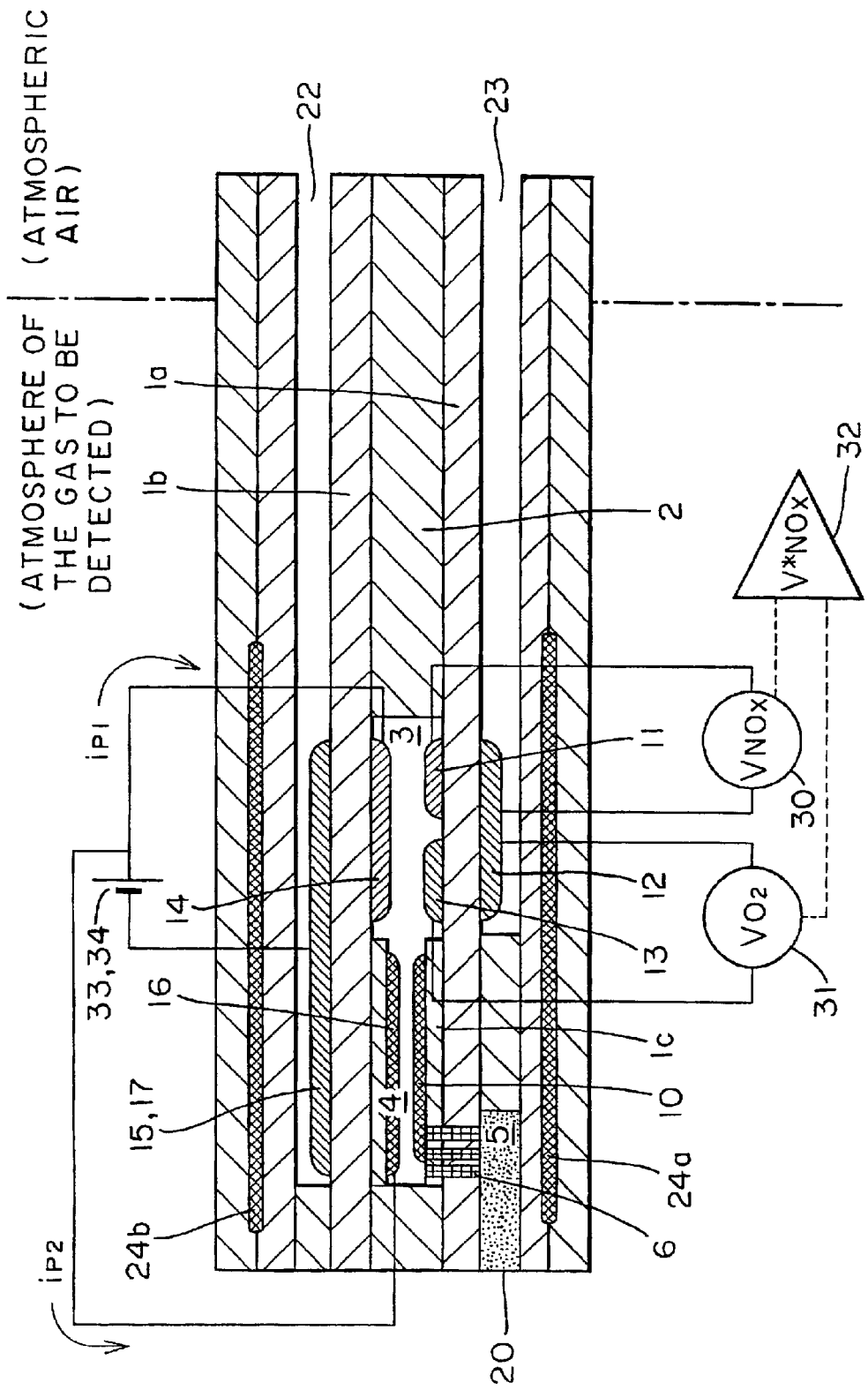
FIG. 12 shows a cross sectional view of another embodiment of the sensor structure according to the first aspect of the present invention.

FIGS. 11 and 12 show structures in which a minute clearance is arranged between the anode electrode 16 of the oxygen supplying pumping cell and a solid electrolyte substrate 1c. In these structures, the first gas treatment chamber 5 can offer the same capability for treating the reducing gases. The clearance is typically set at 5–50 μm. Such structures can reduce performance variations without the necessity for the anode electrode 16 to be porous. Moreover, the formation of a catalyst layer 10 on the solid electrolyte substrate 1c as shown in FIG. 12, allows a further improvement in the capability for oxidizing and removing the reducing gases.

FIG. 13(a) shows a structure in which at least one narrow path, or a gas diffusion path 18, is arranged between anode electrodes 16 of the oxygen supplying pumping cell placed in the second gas treatment chamber 4. It is desirable that the anode electrodes 16 be oxidation catalyst electrodes which are both active to the gases HC and CO to be treated and have oxidation catalyst properties. Here, the oxidation catalyst electrodes 16 need not be porous. It is preferable that the anode electrodes 16 of FIG. 13(a) are configured so that a lead conductor 19 applies a cell voltage to the entire oxidation catalyst electrodes, or anode electrodes 16. It is desirable that an additional protective layer 26 is formed over the gas inlet for long-term stability. The region coated with the protective layer 26 must completely cover the gas inlet 20. The protective layer 26 can be usually formed through the application of porous ceramics such as alumina and the like. FIG. 13(b) is a diagram showing the over view configuration of the gas detection chamber 3.

Figure 14:
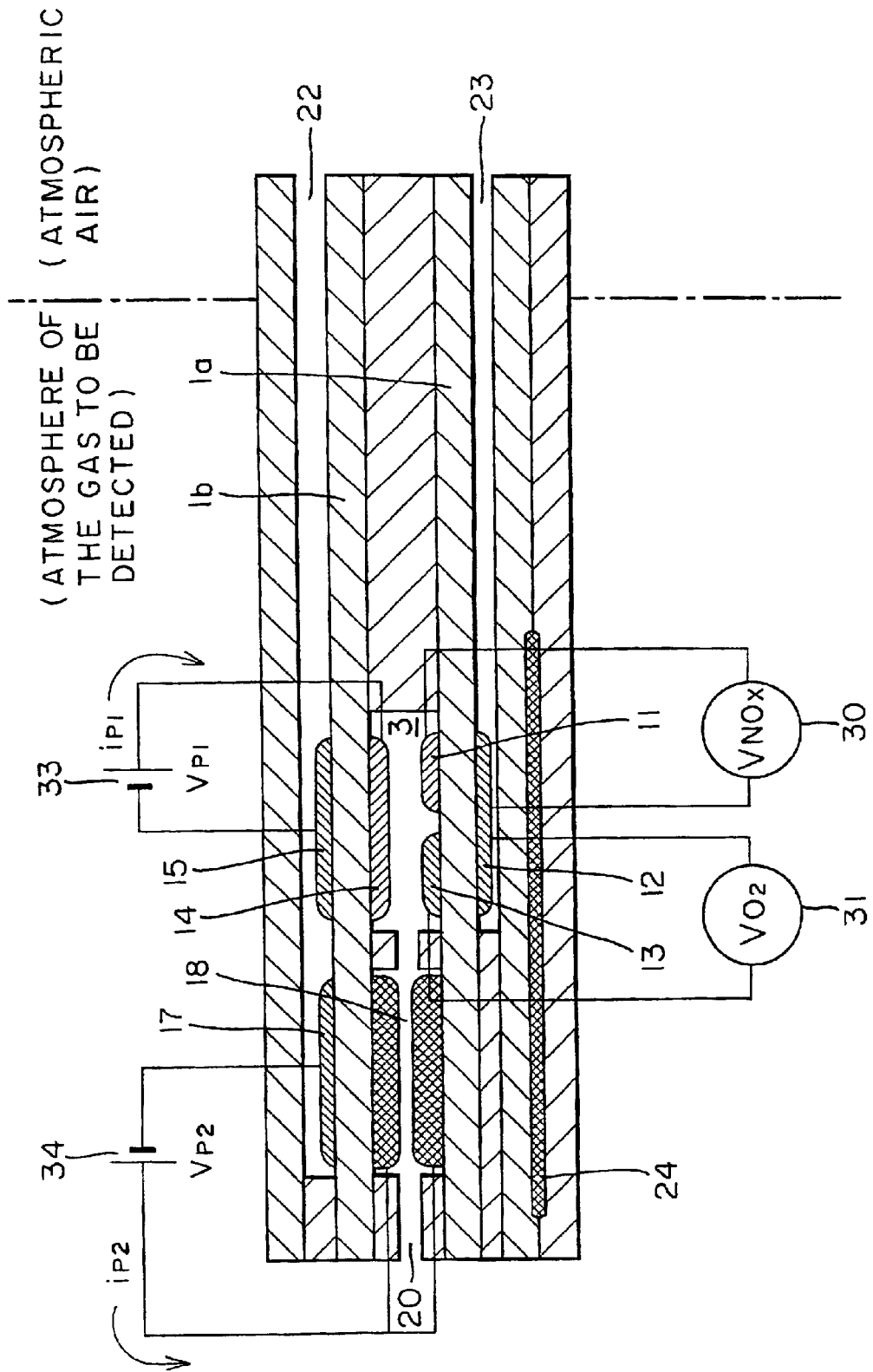
FIG. 14 shows a cross sectional view of another embodiment of the sensor structure according to the second aspect of the present invention.

FIG. 14 shows another embodiment according to the second aspect of the present invention. In this structure, at least one narrow path, or a gas diffusion path, is arranged between oxidation catalyst electrodes placed in the first gas treatment chamber 5. In the embodiment of FIG. 14, a narrow path is formed by the two oxidation catalyst electrodes arranged on the top and bottom of the first gas treatment chamber. Here, the catalyst electrodes need not be porous, but it is desirable that they are porous in terms of performance.

Figure 15A:
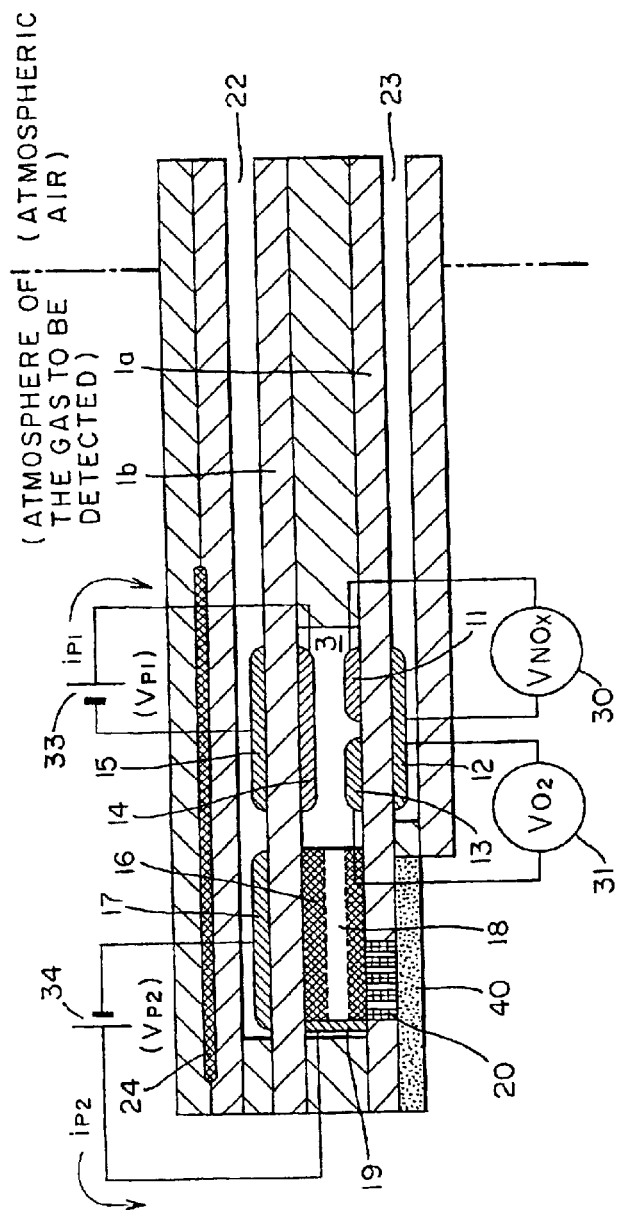
FIG. 15($a$) shows a cross sectional view of another embodiment of the sensor structure according to the second aspect of the present invention, 15($b$) shows a diagram of the over view structure of the detection chamber.
Figure 15B:
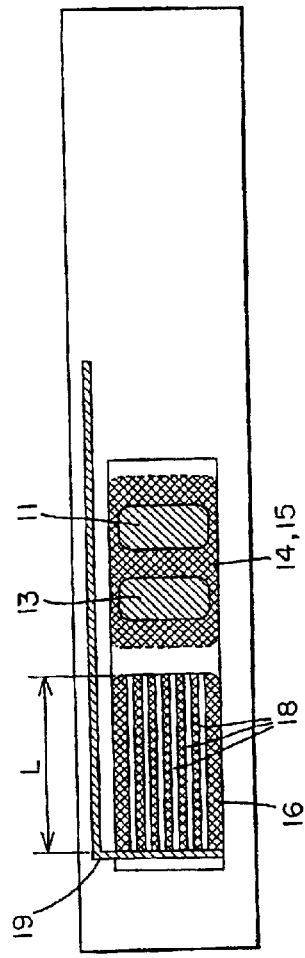

As shown in FIGS. 15(a) and 15(b), at least one slit-like narrow path may be formed in the surface of the oxidation catalyst electrode along the longitudinal direction of the sensor. The ratio of the cross-sectional area S to the diffusion length L of these narrow paths (S/L) is set to a range of 0.001 to 0.1, or preferably 0.005 to 0.05, so as to allow favorable oxidation and removal of the HC reductive gas. Moreover, as in the present structural example, it is desirable that an oxidation catalyst electrode lead 16 be arranged in front of the gas inlet so as not to block the slit-like narrow path. Thereby, even if the lead is of closely packed material, it can drive the oxidation catalyst electrode efficiently over the entire region without interfering with gas diffusion and introduction.

Up to this point, the sensor structures of the present invention have been described. Now, fabrication methods for obtaining the sensors of the present invention will be described. The sensor structures having internal spaces and/or air ducts as described above can be typically obtained by laminating zirconia green sheets under pressure, degreasing them, and then firing them at approximately 1400° C. For oxygen ion conductivity, 3–8 moles of yttria ($Y_2O_3$) is usually added to the green sheets of zirconia ($ZrO_2$). The following is a typical method for fabricating these green sheets. Powdered zirconia with a predetermined amount of yttria additive is mixed with a PVA or other organic binder, a plasticizer, and an organic solvent in a ball mill. Here, a dispersant is sometimes added for better dispersion of the powder particles.

The zirconia slurry obtained thus is formed on a PET film by a doctor blade method into a thickness of several hundreds of micrometers. The resultant is dried until the solvent evaporates and then the resulting sheets can be heated under pressure for strong mutual bonding. In order to create internal spaces in this green laminate, green sheets that form the spaces are perforated, and then filled with, for example, theobromine. This sublimes at a temperature not higher than the degreasing temperature where the organic binder in the green sheets is oxidized and removed.

Meanwhile, the porous member 25 to be loaded into the first gas treatment chamber 5 can also be fabricated of green sheets in the same manner. More specifically, a green sheet comprising mainly zirconia, alumina, or the like is fabricated by the method described above. This green sheet for the porous member can be cut into predetermined sizes and loaded into the first gas treatment chamber for lamination. For a predetermined porosity, the porous member can be adjusted in the particle size of its zirconia, alumina, or the like. The firing conditions can also be appropriately selected for porosity adjustment. In particular, an appropriate degree of porosity of the green sheet obtained from a mixture of powered alumina and powdered silica can be controlled by adjusting the dosage of the silica.

The material of the NOx sensing electrode used in the present invention is not particularly limited as long as it is active to NOx and oxygen. However, due to the high-temperature firing, thermal stability is required. The NOx sensing electrode may use metal oxides such as $NiCr_2O_4$, $MnCr_2O_4$, $FeCr_2O_4$, $Cr_2O_3$, and NiO. The precious metals, Rh, Ir, Pt—Rh alloys, Pt—Ir—Rh alloys, and the like may be used. Solid electrolytes are sometimes dispersed into the NOx sensing electrode to make the electrode more active. These powdered electrode materials, an organic binder, and an organic solvent are mixed into a paste, and applied onto zirconia green sheets by screen printing or other methods.

The anode electrode (NOx conversion electrode 14) of the NOx conversion pumping cell must be active to both oxygen and NOx. For higher ion current, the anode electrode 14 of the NOx conversion pumping cell uses precious metals such as Pt—Rh alloys, Pt—Ru alloys, and Rh. The cathode electrodes 17 and 15 of the oxidation catalyst pumping cell 25, 17, the oxygen supplying pumping cell 16, 17, and the NOx conversion pumping cell 14, 15 typically use Pt. Solid electrolytes are distributed into these electrodes with the aim of increasing active sites.

The driving voltages to the oxidation catalyst pumping cell 25, 17, the oxygen supplying pumping cell 16, 17, and the NOx conversion pumping cell 14, 15 are preferably set at 0.2–0.7 V. Catalysis-given electrodes can drop in oxidation removal efficiency if the set voltages are either too high or too low. That is, the voltage applied to the oxidation catalyst electrode may be set to 0.2–0.7 V, and preferably 0.3–0.5 V.

When the voltage to the oxygen supplying pumping cell is made identical to that of the NOx conversion pumping cell, the cathode electrode 17 of the oxidation catalyst pumping or oxygen supplying pumping cell and the cathode electrode 15 of the NOx conversion pumping cell can be combined with each other. This allows a configuration in which the driving power supply is also shared with the NOx conversion pumping cell. Here, the pumping cell voltage can be well determined from the total performance of the NOx conversion efficiency and the reducing gas removal efficiency.

Hereinafter, further details will be described with reference to embodiments. It should be understood that the present invention is not limited to these embodiments, and is intended to cover all those derived from the same concept of the present invention.

EXAMPLE 1

A NOx sensor device having the sensor structure shown in FIG. 1 was fabricated in the following manner. Firstly, a zirconia green sheet with an yttria additive of 6% by mole was fabricated by the above-mentioned doctor blade method. This zirconia green sheet was approximately 200 µm in thickness. This green sheet was cut into the pre-fire sizes of the sensor substrates, and simultaneously perforated at points for forming the gas detection chamber 3, the first gas treatment chamber 5, and the air introducing duct 22. A green sheet intended for the porous member 25 to be loaded into the first gas treatment chamber was fabricated from alumina with a silica additive of 10% by weight. Electrodes, lead conductors, heaters, and the like were printed on the respective cut green sheets in a screen printer.

The cathode electrode 15 of the NOx conversion pumping cell, the reference electrode 12 of the NOx sensing cell, and the heater 24 were printed with a Pt paste. The NOx sensing electrode 11 was formed of an oxide paste of $NiCr_2O_4$. The individual green sheets printed with these pastes were successively stacked with Pt wires inserted in the lead portions so as to form the laminated structure of FIG. 1, and then laminated in hot water with a hydrostatic press. This laminate was degreased at approximately 500° C., followed by firing in a high temperature atmosphere of 1400° C.

The sensor device fabricated was set into a characteristic measurement holder, and connected to the measuring circuit and control circuit shown in FIG. 1 for sensor characteristic evaluations. More specifically, a constant voltage of 0.5 V was applied to the NOx conversion pumping cell with the NOx conversion electrode 14 as the anode electrode and the NOx conversion counter electrode 15 as the cathode electrode. At the same time, the potentiometer 30 having an input impedance of 10 MΩ or higher was connected between the NOx sensing electrode 11 and the reference electrode 12.

Figure 16:
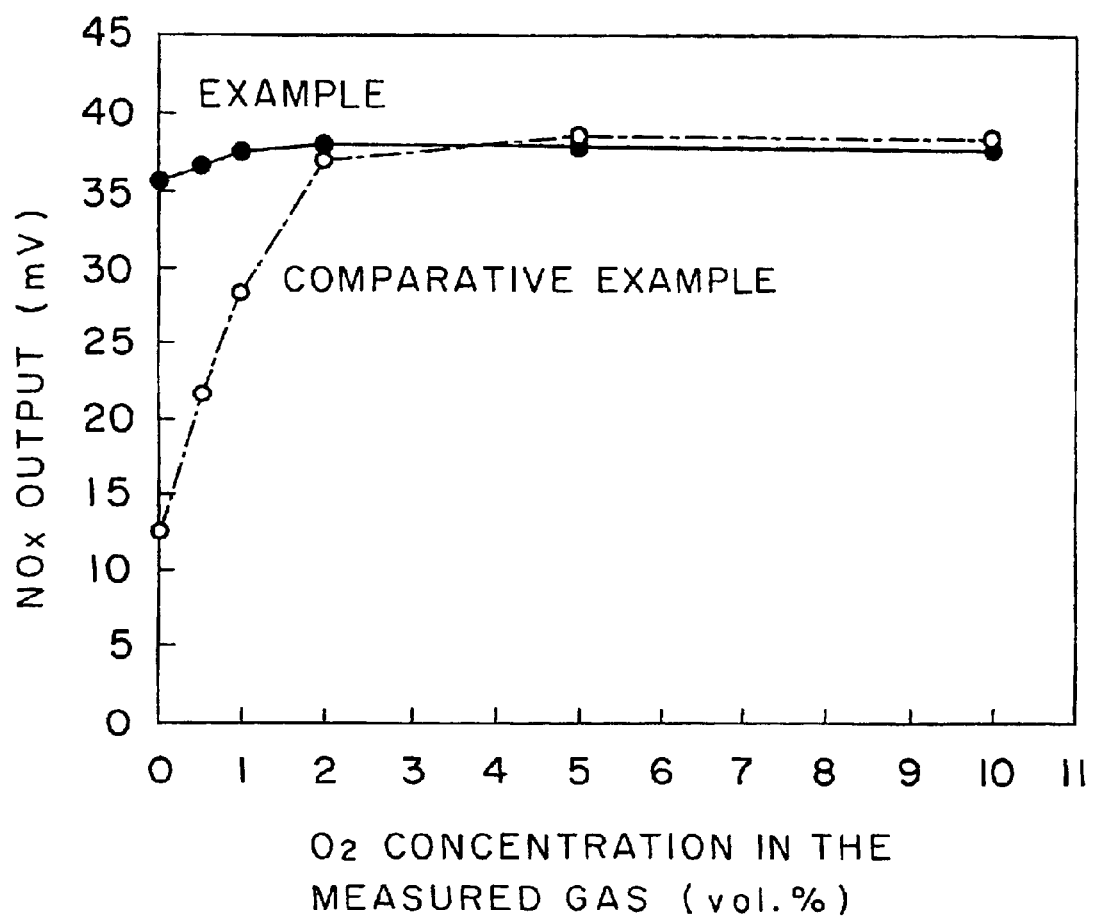
FIG. 16 shows the oxygen concentration dependency of the sensor output with a NO concentration of 100 ppm.

Although not shown in FIG. 1, a circuit for measuring the bulk impedance of the zirconia substrate interposed between the NOx conversion electrode 14 and the NOx conversion counter electrode 15 was connected in parallel to obtain a sensor temperature signal. This signal was connected to a temperature control circuit connected between two leads of the heater so that the sensor was controlled to a predetermined temperature. Here, the sensor output with respect to NO was measured by using mixed gas as the measured gas containing 100-ppm NO, oxygen, nitrogen, water vapor, and 5000-ppm $C_3H_8$ (propane). The oxygen concentration in the measured gas ranged 0–20% by volume. The concentration of water vapor was constant at 10% by volume. FIG. 16 shows the oxygen concentration dependency of the sensor output with a NO concentration of 100 ppm here.

As a comparative example, a comparative sample device A with no member in the first gas treatment chamber was prepared in the same manner. As is evident from FIG. 16, in the sample device of the present example (marked with ● in the chart), a drop in the sensor output is significantly suppressed even if the oxygen concentration in the measured gas falls to or below 1% by volume. In other words, it is clear that the sample device of the present example offers a generally constant NOx output without influence of the reducing gas (propane) even when oxygen is absent in the measured gas. This suggests that $C_3H_8$ in the measured gas was oxidized and removed by the sensor structure of the present invention.

On the other hand, in the comparative example A (marked with ○ in FIG. 16), the NOx output drops with decreasing oxygen concentration when the oxygen concentration in the measured gas falls to or below 2% by volume. This shows that in the conventional sample device, $C_3H_8$ in the measured gas was not removed completely.

EXAMPLE 2

As in the example 1, a NOx sensor having the oxidation catalyst pumping cell shown in FIG. 2 was fabricated. The cathode electrodes 17 and 15 of the oxidation catalyst pumping cell and the NOx conversion pumping cell, the reference electrode 12, and the heater 24 were printed using a Pt paste. The oxidation catalyst electrode 25 was formed of a Pt—Pd (5 wt %) alloy paste. Here, for the purpose of adjusting the electrode porosity, powdered zirconia solid electrolyte was added to the Pt—Pd (5 wt %) alloy paste so as to occupy approximately 20% of the post-fired electrode by volume.

Figure 17:
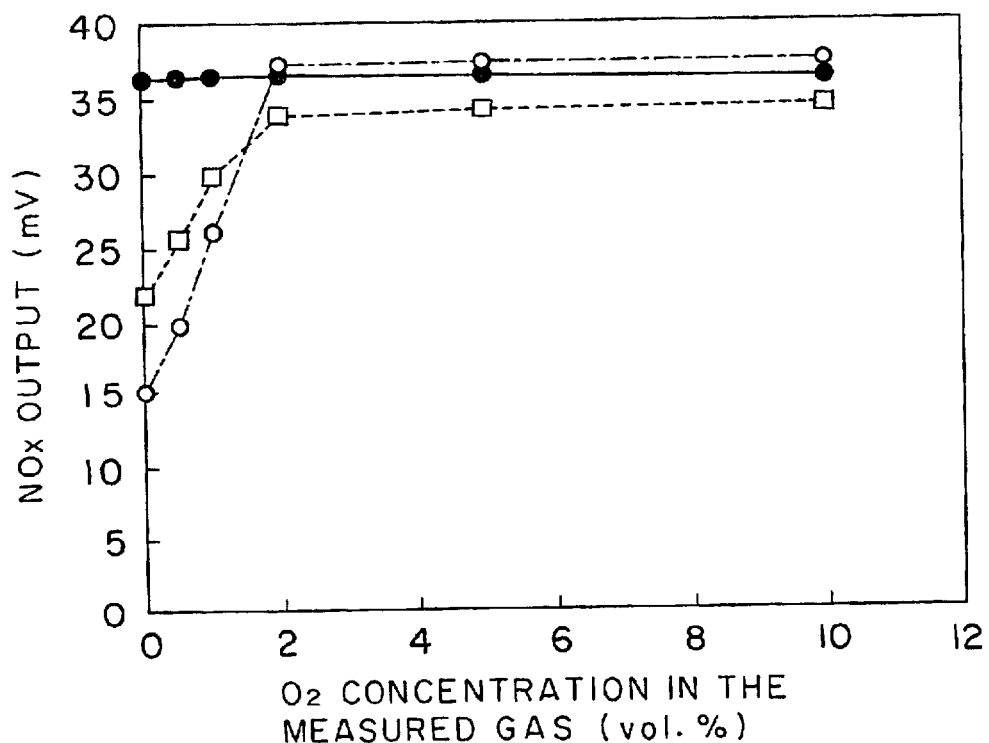
FIG. 17 shows the oxygen concentration dependency of the sensor output with a NO concentration of 100 ppm.

The sensor sample fabricated thus was set into a measurement holder, and connected to the measuring circuit and control circuit shown in FIG. 2 for sensor characteristic evaluations. More specifically, the D.C. voltage source 34 was connected between the oxidation catalyst electrode 25 and its counter electrode 17. A constant voltage of 0.4 V was applied with the counter electrode 17 as the negative electrode (cathode) and the oxidation catalyst electrode 25 as the positive electrode (anode). Meanwhile, the D.C. power supply 33 was connected between the NOx conversion electrode 14 and its counter electrode 15. A constant voltage of 0.5 V was applied with the counter electrode 15 as the negative electrode (cathode) and the NOx conversion electrode 14 as the positive electrode (anode). At the same time, the potentiometer 30 having an input impedance of 10 MΩ or higher was connected between the NOx sensing electrode 11 and the reference electrode 12. Although not shown in FIG. 2, a circuit for measuring the bulk impedance of the zirconia substrate between the NOx conversion electrode 14 and the NOx conversion counter electrode 15 was connected in parallel to obtain a sensor temperature signal. This signal was connected to a temperature control circuit connected between two leads of the heater substrate, so that the sensor temperature was controlled to 650° C. Here, the sensor output with respect to NO was measured by using a (nitrogen-based) mixed gas as the measured gas containing 100 ppm NO, oxygen, water vapor, and hydrocarbon gas, or 5000 ppm $C_3H_6$. The oxygen concentration in the measured gas ranged 0–20% by volume. The concentration of water vapor was constant 10% by volume. FIG. 17 shows the oxygen concentration dependency of the sensor output with 100 ppm NO. As comparative examples, a sample A without the above-described catalytic electrode and a sample B having a first gas treatment chamber loaded with a catalyst of a Pt—Pd(5 wt %) alloy were provided. The measurements are also shown in FIG. 17. As is evident therefrom, the sample device of the present example (marked with ● in the chart) offers a generally constant sensor output even when the oxygen concentration in the measured gas falls to zero. In other words, it is clear that the sample device of the present example offers the generally constant NOx output even if oxygen is absent from the measured gas. This shows that the $C_3H_6$ in the measured gas was oxidized and removed by the sensor structure of the present invention. On the other hand, in comparative example A (marked with ○ in the chart) and comparative example B (marked with □ in the chart), the NOx outputs drop with an decreasing concentration of $O_2$ when the oxygen concentration in the measured gas falls to or below 2%. This shows that the conventional sample devices were far from perfect with respect to removal of $C_3H_6$ from the measured gas.

EXAMPLE 3

Figure 18:
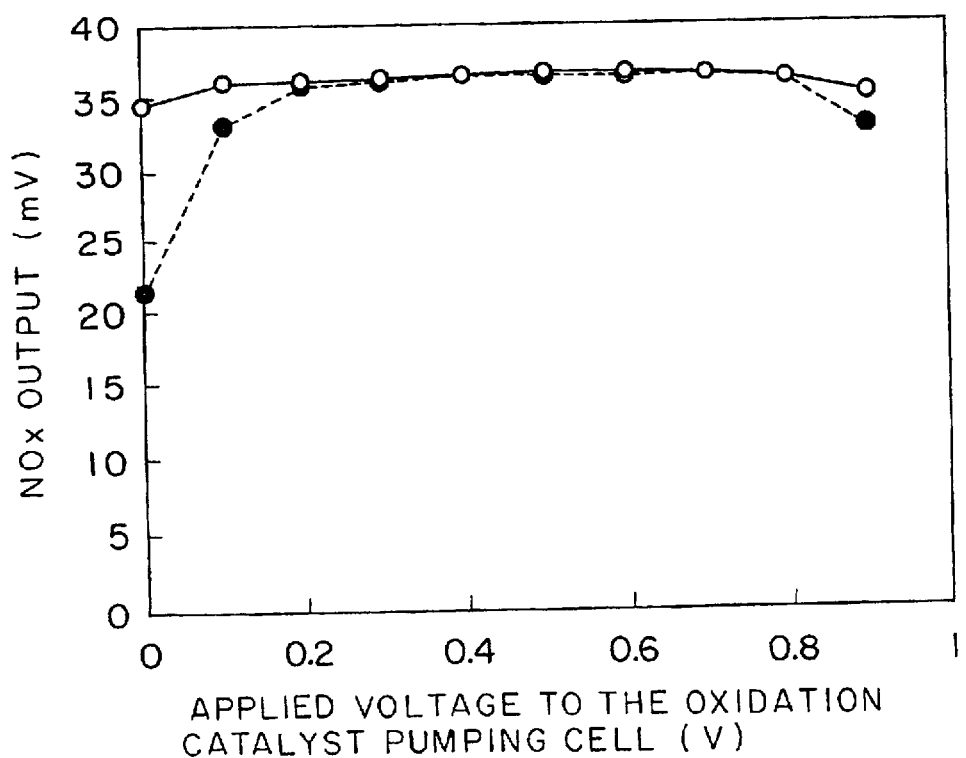
FIG. 18 shows a graphical representation of relationships between the applied voltage to the oxidation catalyst cell and NOx output with a NO concentration of 100 ppm.
Figure 19:
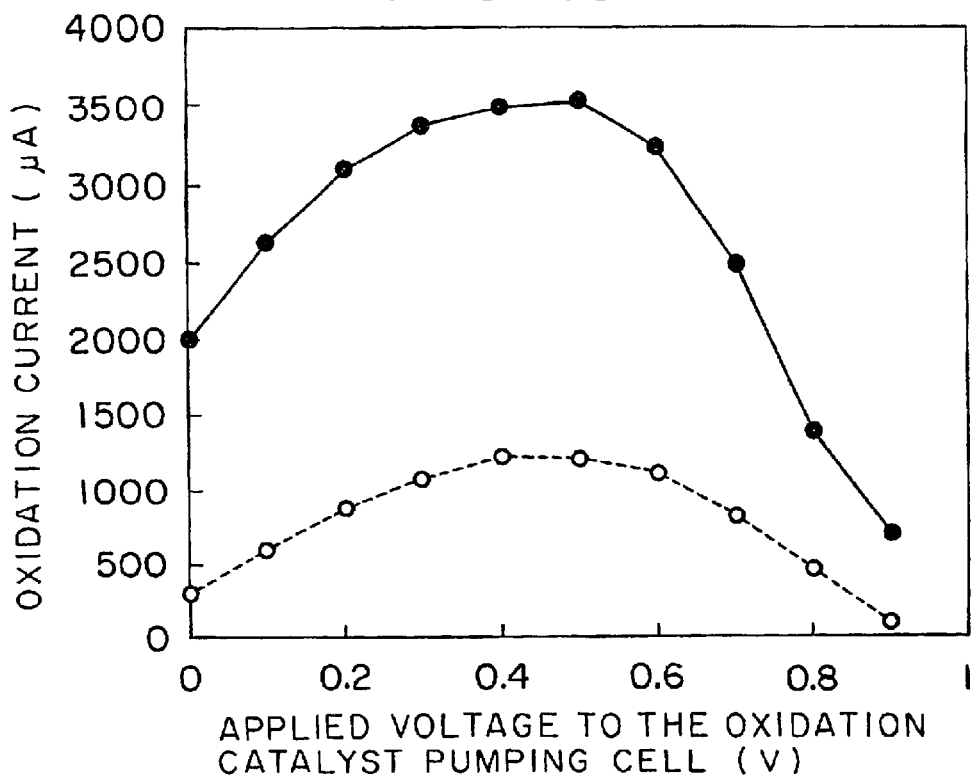
FIG. 19 shows a graphical representation of relationships between the applied voltage to the oxidation catalyst cell and the oxidation current.

The same sample sensor device used in the example 2 was fabricated, and evaluated while changing the driving voltage to the oxidation catalyst pumping cell in the range of 0–0.9 V. That is, the oxidation catalyst electrode was checked for the voltage dependency of the electrochemical effect, which had been found in the example 2. Here, the oxygen concentration in the measured gas was set to 0% and 5%. In the meantime, for the purpose of evaluating the HC oxidation performance of the oxidation catalyst electrode, the oxidation catalyst pumping cell was also evaluated for the dependency of a HC oxidation current on the cell voltage. Here, the HC oxidation current was a difference between the base currents in the presence and absence of HC. That is, the greater the oxidation current, the higher the capability for oxidizing and removing reducing gases. FIGS. 18 and 19 show the measurements. In FIGS. 18 and 19, the data marked with ● was at an oxygen concentration of 0%, and the data marked with ○ was at an oxygen concentration of 5%. It is evident that the oxidation current of the oxidation catalyst electrode, or the oxidation removal capability has a dependence on the cell voltage. It is also found that the oxidation removal capability is in clear related to the oxidation current. The result is that the oxidation catalyst voltage can be set at 0.1–0.8 V, or preferably 0.2–0.7 V, to sufficiently oxidize and remove a high concentration of HC even in completely fuel rich atmospheres.

EXAMPLE 4

Figure 20:
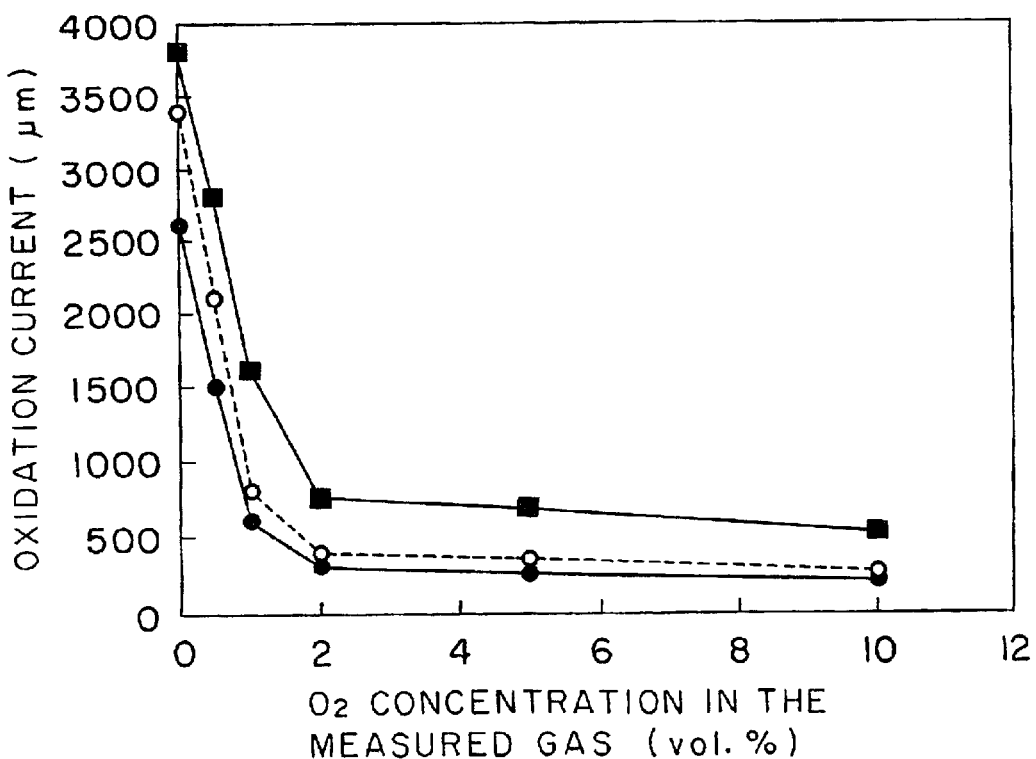
FIG. 20 shows a graphical representation of relationships between the oxygen concentration in the measured gas and the oxidation current.

The same sample sensor device used in the example 2 was used to check for the relation between the oxidation current of the oxidation catalyst pumping cell and the oxygen concentration in the measured gas. Here, the concentration of $C_3H_6$ was set at 1000 ppm (marked with ● in the chart), 2000 ppm (marked with ○ in the chart), and 5000 ppm (marked with ■ in the chart). The driving voltage of the catalyst electrode pumping cell was 0.5 V. The other measured conditions were the same as those of the example 2. FIG. 20 shows the measurements. It is found that the oxidation current increases with an increasing concentration of $C_3H_6$. The oxidation current also increases with a decreasing oxygen concentration of the measured gas. In particular it can be seen that the oxidation current increases abruptly at oxygen concentrations lower than or equal to 1%. This confirms that the oxidation catalyst electrode ensures the oxidation removal capability even in a measured gas of lower oxygen concentration.

EXAMPLE 5

Sample sensor devices having the structures of FIGS. 4 and 5 were fabricated as in the example 2. Here, the oxidation catalyst electrodes were fabricated from the materials shown in Table 1. These samples were used to examine the influences of the oxidation catalyst electrode materials on the NOx output in each of the sensor structures. Here, with the measured gas set at a 0% oxygen concentration by volume, ratios were determined between sensitivity in the presence and absence of hydrocarbon gas, or $C_3H_8$ of 5000 ppm. Table 1 collectively shows the results. High sensitivity ratios (sensitivity in the presence of $C_3H_8$/sensitivity in the absence of $C_3H_8$) can be seen in all cases. Since no sensitivity drop is found as in the comparative example of the example 2, HC is assumed to be oxidized and removed completely. It is also shown that the sensor structure of FIG. 5 offers superior sensitivity ratios compared to the sensor structure of FIG. 4.

TABLE 1

| Material for oxidation catalyst electrode | Sensitivity ratio with 100-ppm NO of sensor having structure of FIG. 4 | Sensitivity ratio with 100-ppm NO of sensor having structure of FIG. 5 |
| --- | --- | --- |
| Pt | 0.986 | 0.992 |
| Pd | 0.992 | 0.993 |
| Au | 0.973 | 0.986 |
| Ir | 0.984 | 0.989 |
| Rh | 0.975 | 0.980 |
| Pt—Pd (5 wt %) | 0.990 | 0.992 |
| Pt—Au (5 wt %) | 0.989 | 0.990 |
| Pt—Ir (5 wt %) | 0.987 | 0.990 |
| Pt—Rh (5 wt %) | 0.976 | 0.981 |
| Au—Pd (10 wt %) | 0.982 | 0.984 |
| Ir—Au (10 wt %) | 0.978 | 0.983 |
| Ir—Pd (5 wt %) | 0.991 | 0.994 |
| Ir—Rh (5 wt %) | 0.984 | 0.984 |
| NiO—Pt (10 wt %) | 0.990 | 0.993 |
| $Cr_2O_3$—Pt (10 wt %) | 0.989 | 0.990 |
| $WO_3$—Pt (10 wt %) | 0.981 | 0.988 |
| $NiCr_2O_4$—Pt (10 wt %) | 0.976 | 0.984 |
| $Ir_2O_3$—Pt (10 wt %) | 0.985 | 0.988 |
| PdO—Pt (10 wt %) | 0.992 | 0.993 |
| $RhO_2$—Pt (10 wt %) | 0.983 | 0.986 |

EXAMPLE 6

Sample sensor devices having the sensor structure shown in FIG. 5 were fabricated as in the example 2. In the present example, for the purpose of adjustments to the porosities of the oxidation catalyst electrodes the samples were fabricated with the dosage of the zirconia solid electrolyte changed as shown in Table 2. After the tests, the samples were disassembled and checked for the voidages of the respective oxidation catalyst electrodes. Table 2 shows the results of the examinations with respect to the influence of the presence of $C_3H_8$ (5000 ppm) upon the NOx sensitivity. It can be seen that electrode voidages in the range of 9.7–41.0% by volume, or preferably 18.4–41.0% by volume, satisfy both the sensitivity ratio and the responsivity at the same time. Here, solid electrolyte of 10–40% by volume is preferably added to the electrode.

TABLE 2

| Porosity of the oxidation catalyst electrode (vol %) | Amount of zirconia (vol %) | Sensitivity ratio with 100-ppm NO | Responsivity |
| --- | --- | --- | --- |
| 5.3 | 5 | 0.995 | X |
| 9.7 | 10 | 0.994 | ○ |
| 18.4 | 20 | 0.991 | ⊙ |
| 31.6 | 30 | 0.988 | ⊙ |
| 41.0 | 40 | 0.981 | ⊙ |
| 48.5 | 50 | 0.953 | ⊙ |

EXAMPLE 7

Figure 21:
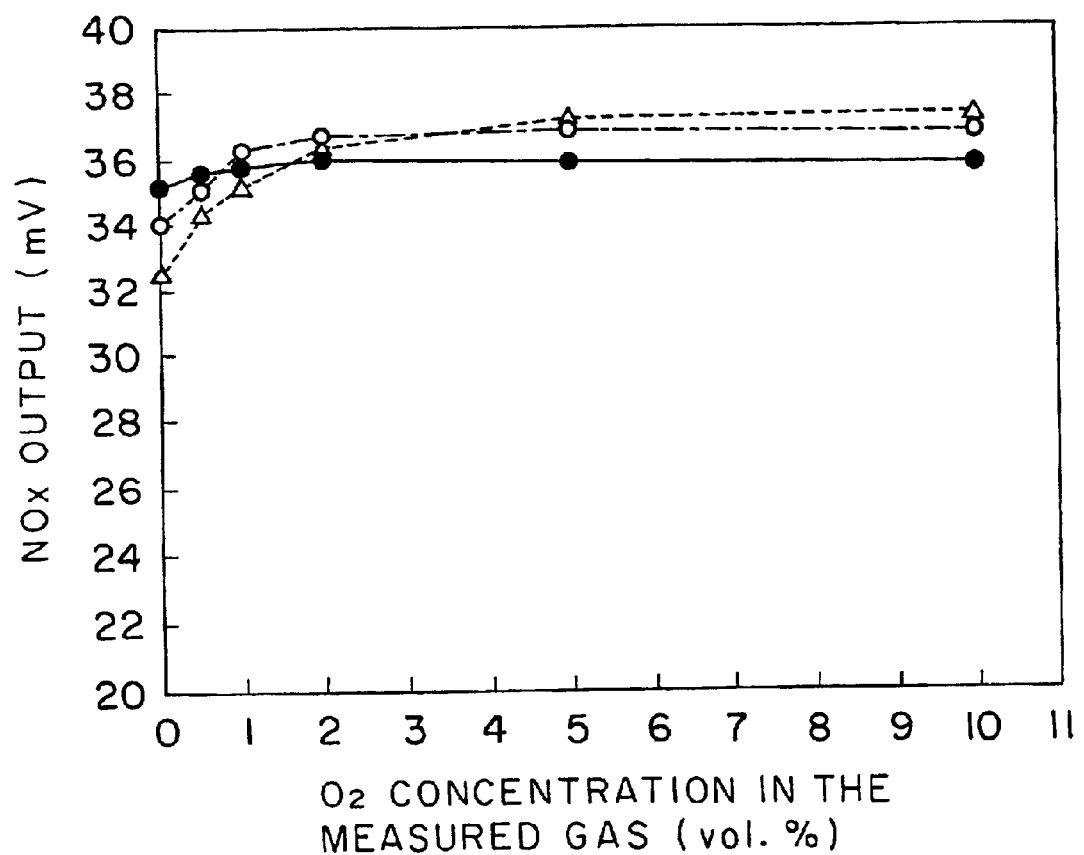
FIG. 21 shows the oxygen concentration dependency of the sensor output with a NO concentration of 100 ppm.

Sample sensor devices having sensor structures with the oxygen supplying pumping cells of FIGS. 7 and 8 were fabricated as in the example 1. The electrodes 16 and 17 of the oxygen supplying pumping cells were formed of Pt, and a cell voltage of 0.5 V was applied thereto. These samples were subjected to the same evaluations as those of the example 1. In the present example, the measured gas contained 5000 ppm of $C_3H_6$ and 10000 ppm of CO as reducing gases. Moreover, the sensor device of FIG. 1 not having the oxygen supplying pumping cell (marked with Δ in the chart) was also provided for comparison. FIG. 21 shows the measurements. The following can be seen from the sensor device of FIG. 7 (marked with ○ in the chart) and the sensor device of FIG. 8 (marked with ● in the chart). That is, the device structures in which the second gas treatment chamber 4 incorporates the oxygen supplying pumping cell offer more stable sensor outputs with little influence from the reducing gases. It is also found from the results that the device structure of FIG. 8, having the second gas treatment chamber loaded with the anode electrode 16 of the oxygen supplying pumping cell, undergoes the least influence from the reducing gases.

EXAMPLE 8

Figure 22:
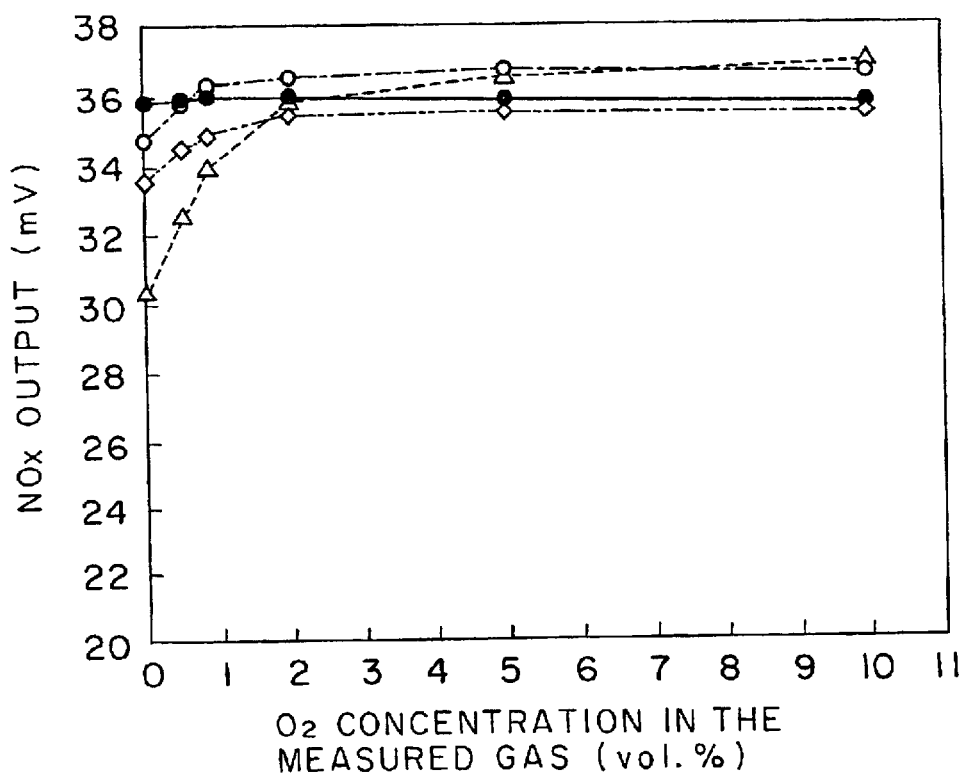
FIG. 22 shows the oxygen concentration dependency of the sensor output with a NO concentration of 100 ppm.

Sample sensor devices having sensor structures of FIGS. 9, 11, and 12, incorporating the oxygen supplying pumping cell and arranging the first gas treatment chamber in a separate layer, were fabricated as in the example 1. The electrodes 16 and 17 of the oxygen supplying pumping cells were formed of Pt, and a cell voltage of 0.5 V was applied thereto. These samples were subjected to the same evaluations as those of the example 1. In the present example, the measured gas contained 5000 ppm of $C_3H_8$, 20000 ppm of CO, and 2000 ppm of $H_2$ as reducing gases. Moreover, the sensor device of FIG. 1 (marked with Δ in the chart) was also provided for comparison. FIG. 22 shows the measurements. The following is found from the sensor device of FIG. 9 (marked with ● in the chart), the sensor device of FIG. 11 (marked with ◇ in the chart), and the sensor device of FIG. 12 (marked with ○ in the chart). That is, in the sensor devices in which the second gas treatment chamber 4 incorporates the oxygen supplying pumping cell and the first gas treatment chamber is arranged in a separate layer, the sensor outputs are more stable with little influence from the reducing gases.

EXAMPLE 9

Sample sensor devices having the structure of FIG. 9 were fabricated as in the example 1. In the present example, the porous members 25 had the porosities shown in Table 3. These samples were used to examine the influence of the porosity on the NOx output. The NOx in the measured gas was NO of 100 ppm. The oxygen concentration was 0% by volume. $C_3H_8$ of 5000 ppm and CO of 30000 ppm coexisted as the reducing gases. Here, comparisons were made between the sensor outputs ($E_r$) in the presence of the reducing gases and the sensor outputs ($E_0$) in the absence of the reducing gases to check the reducing gas removal efficiency in the porous members 25 with various porosities. Table 3 shows the calculations of the rates of change of the sensor outputs, or the ratios of the differences ($E_r - E_0$) between the sensor outputs in the presence and absence of the reducing gases to the sensor outputs ($E_0$) in the absence of the reducing gases. In addition, relative evaluations on the sensor responsivity (response speed) are also collectively shown in Table 3. The porosities of the porous members are measurements obtained from disassembling real samples.

TABLE 3

| Porosity of the porous member (%) | $(E_r - E_0)/E_0$ (%) | response speed |
|---|---|---|
| 1.7 | −0.1 | X |
| 3.1 | −0.1 | X |
| 4.6 | −0.2 | Δ |
| 9.4 | −0.3 | ○ |
| 11.5 | −0.4 | ○ |
| 22.4 | −0.6 | ○ |
| 30.3 | −0.7 | ○ |
| 41.8 | −1.2 | ○ |
| 48.5 | −5.9 | ○ |
| 60.2 | −12.4 | ○ |

It is found from the results that porous members with lower porosities have lower rates of change of the sensor outputs, therefore efficiently removing the reducing gases. It is also confirmed that the rates of change of the sensor outputs increase and the reducing gas removal efficiencies decrease as the porous members increase in porosity. On the other hand, the sensor response speed is low in porous members with lower porosities, whereas it is improved by an increase in porosity. In terms of both the reducing gas removal efficiency and the responsivity, the porosity of the porous member in the present invention may be set within a range of 4.6% and 41.8%, and preferably 9.4% and 30.3%.

EXAMPLE 10

Sample sensor devices having the structure of FIG. 1 were fabricated as in the example 1. In the present example, the porous members 25 had a constant porosity of approximately 15%, whereas they carried various types of catalyst shown in Table 4. Each catalyst was carried in an amount of 3 mg/cm$^3$. These samples were used to examine the influence the type of the catalyst carried by the porous member has upon the NOx output. Again, the NOx in the measured gas was NO of 100 ppm. The oxygen concentration was 0% by volume. $C_3H_8$ of 5000 ppm and CO of 10000 ppm coexisted as the reducing gases. The sensor outputs with and without these reducing gases were compared. Moreover, for the purpose of comparison with the present example, a sample carrying no catalyst was likewise fabricated. Table 4 collectively shows the results. It is clear that the porous members carrying the catalysts shown in Table 4 further promote the removal of the reducing gases.

TABLE 4

| Material for catalyst | $(E_r - E_0)/E_0$ (%) |
|---|---|
| — | −12.8 |
| Pt | −3.7 |
| Pd | −4.8 |
| Ir | −5.1 |
| Au | −6.3 |
| Ru | −4.6 |
| Ag | −4.3 |
| Rh | −3.2 |

EXAMPLE 11

Figure 23:
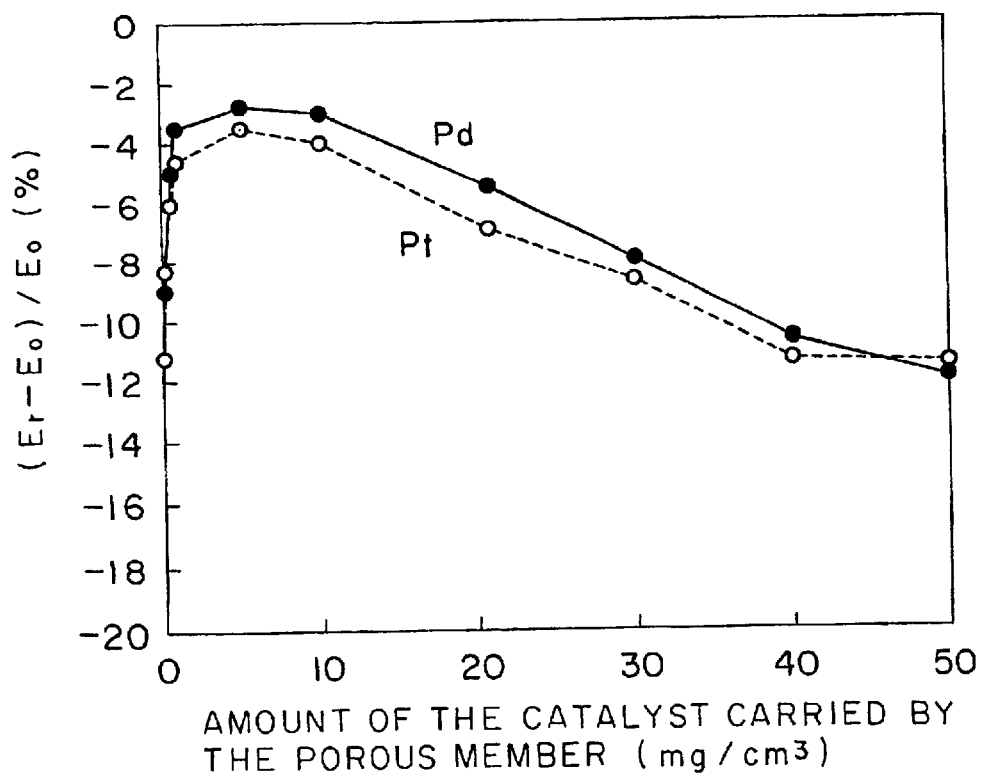
FIG. 23 shows a graphical representation of relationships between the amount of the catalyst carried by the porous member and $(E_r-E_0)/E_0$.

Sample sensor devices having the structure of FIG. 1 were fabricated as in the example 10. In the present example, the porous members 25 had a constant porosity of approximately 15% while carrying Pt or Pd as their catalyst. Each catalyst was carried in amounts of 0, 0.1, 0.5, 1, 5, 10, 20, 30, 40, and 50 mg/cm$^3$. These samples were used to examine the influence of the type and amount of the catalyst carried by the porous member upon the NOx output. Again, the NOx in the measured gas was NO of 100 ppm. The oxygen concentration was 0% by volume. $C_3H_8$ of 5000 ppm and CO of 10000 ppm coexisted as the reducing gases. The sensor outputs with and without these reducing gases were compared. FIG. 23 shows the results of the present embodiment. It is clear that either type of catalyst offers greater effects when carried in amounts of 0.1–30 mg/cm$^3$. It is also seen that the carried amounts of 0.5–10 mg/cm$^3$ provide significant effects.

EXAMPLE 12

Sample sensor devices having the structure of FIG. 1 were fabricated as in the example 10. In the present example, the catalyst carriers, or the porous members 25, were made of zeolite (A), activated zirconia, or activated alumina. Minute quantities of inorganic binder were added to powders of these carrier materials before press forming. Then, the resultants were cut into predetermined sizes and temporarily fired at 700° C. to become catalyst carrying pellets. Then, catalysts of Pt, Rh, Pt—Rh (50 wt %), and Pt—Pd (50 wt %) were carried by means of their acid solutions. Each sample carried approximately 3 mg/cm$^3$ of catalyst. The carrier pellets thus carrying their respective catalysts were loaded into the first gas treatment chambers 5 of fired sample devices with preformed spaces, to make the samples of the present example. As in the example 10, these samples were evaluated for performance. Table 5 shows the results. The large suppression of the sensor output drop in each sample shows a high catalyst effect.

In particular, the carriers of zeolite maintain favorable sensor outputs irrespective of the catalyst materials. The zirconia carrier carrying the Rh catalyst also maintains a favorable sensor output.

TABLE 5

| Material for catalyst carrier | $(E_r - E_0)/E_0$ (%) | | | |
|---|---|---|---|---|
| | Pt | Rh | Pt + Rh | Pt + Pd |
| Zeolite | −1.9 | −1.1 | −1.2 | −1.6 |
| Activated zirconia | −3.2 | −1.1 | −1.3 | −2.9 |
| Activated alumina | −2.5 | −1.7 | −1.6 | −2.2 |

EXAMPLE 13

Sample sensor devices having the structure of FIG. 1 were fabricated as in the example 12. In the present example, the catalyst carriers, or the porous members 25, were made of activated alumina. A solid solution of zirconia and ceria was carried with high dispersion. The following provides the carrying method. Initially, an aqueous solution of cerous chloride and zirconium oxychloride was prepared, and neutralized with ammonia water for co-precipitation. The resultant was dried and fired to obtain a powered zirconia/ceria solid solution of high activity (high specific surface). Here, zirconia and ceria had a composition ratio of 50:50 (by mole). Powdered activated alumina and an inorganic binder were added to this powdered solid solution to fabricate a pellet-like porous member. Here, the powdered solid solution and the activated alumina had a weight ratio of 60:40 (wt %). This porous pellet was impregnated with an aqueous solution of rhodium chloride, and dried into a sample device.

Here, Rh was carried in an amount of 4.5 mg/cm$^3$ with respect to the space volume of the first gas treatment chamber. The carrier pellet thus carrying the catalyst was loaded into the first gas treatment chamber 5 of fired sample device with a preformed space, to make a first sample of the present embodiment. Like the first sample, a second sample was made of a powdered ceria/zirconia solid solution of high activity. This powdered solid solution and activated alumina together with powdered zeolite (A) were mixed and fired at 700° C. to obtain a porous pellet, which was loaded into a sensor device. The amount of zeolite added at this point was 40% of the porous pellet by weight. Here, the ceria/zirconia solid solution functions as not only a catalytic oxide but also a carrier for carrying the precious metal.

As in the example 10, these samples were evaluated for performance. Table 6 shows the results. The significant suppression of the sensor output drops in the first and second samples indicates high catalyses. In particular, the zeolite-added carrier shows little drop in the sensor output.

TABLE 6

| Sample | $(E_r - E_0)/E_0$ (%) |
|---|---|
| First sample | −0.7 |
| Second sample | −0.2 |

EXAMPLE 14

Samples having the sensor structure shown in FIGS. 15(a) and 15(b) were fabricated as in the example 2. In the present example, the cross-sectional areas of the gas diffusion paths 18 formed in the oxidation catalyst electrodes were changed so as to adjust the diffusion resistances of the gas diffusion paths 18. Moreover, the devices were cut under a scanning electron microscope (SEM), and the cross-sectional areas of the individual narrow paths were examined to calculate the total cross-sectional areas and diffusion resistances (S/L). These sample devices with different diffusion resistances were used to check the influence of the coexisting $C_3H_8$ (5000 ppm) on the NOx sensitivity. Table 7 shows the results. It can be seen that the diffusion resistances of the gas diffusion paths 18, when set to the range of 0.001–0.1 or preferably 0.005–0.05, at the same time satisfy both the sensitivity ratio and the responsiveness.

TABLE 7

| Diffusion resistance (S/L) | Sensitivity ratio | Response speed |
|---|---|---|
| 0.0006 | 0.992 | X |
| 0.0012 | 0.995 | ○ |
| 0.0032 | 0.992 | ○ |
| 0.0057 | 0.990 | ◎ |
| 0.019 | 0.992 | ◎ |
| 0.037 | 0.987 | ◎ |
| 0.053 | 0.980 | ◎ |
| 0.084 | 0.828 | ◎ |
| 0.109 | 0.762 | ◎ |

While there has been described what are at present considered to be preferred embodiments of the invention, it will be understood that various modifications may be made thereto, and it is intended that the appended claims cover all such modification as fall within the true spirit and scope of the invention.

As many apparently widely different embodiments of the present invention can be made without departing from the spirit and scope thereof, it is to be understood that the invention is not limited to the specific embodiments thereof except as defined in the appended claims.

What is claimed is:

1. A NOx sensor comprising:
   a gas detection chamber composed of an internal space formed by a first zirconia solid electrolyte substrate having oxygen ion conductivity, an opposed second zirconia solid electrolyte having oxygen ion conductivity, and a spacer separating said zirconia solid electrolyte substrates;
   a NOx sensing cell including a NOx sensing electrode fixed onto one side of said first zirconia solid electrolyte substrate in said gas detection chamber, said NOx sensing electrode being active to NOx and oxygen, and a reference electrode fixed onto the other side of said first zirconia solid electrolyte substrate, said reference electrode being active to at least oxygen;
   a NOx conversion pumping cell including a NOx conversion electrode fixed onto said second zirconia solid electrolyte substrate in said gas detection chamber, said NOx conversion electrode being active to NOx and oxygen, and a counter electrode to be paired with said NOx conversion electrode, said counter electrode being fixed onto said second zirconia solid electrolyte substrate, being active to oxygen;
   voltage applying means for applying a predetermined voltage to said NOx conversion pumping cell;
   a first gas treatment chamber disposed between said gas detection chamber gas inlet leading to an atmosphere of a gas to be detected;
   an inorganic porous member with a porosity of 5–40% by volume being loaded into only said first gas treatment chamber; and
   means for measuring a potential difference between said NOx sensing electrode and said reference electrode while converting NOx in the gas to be detected into single component after a reducing gas in the gas to be detected is oxidized in said first gas treatment chamber, and thereby detecting a total NOx concentration in the gas to be detected.

2. The NOx sensor according to claim 1, wherein an oxygen supplying pumping cell for supplying oxygen to at least said first gas treatment chamber is arranged between said first gas treatment chamber loaded with said porous member and said gas detection chamber containing said NOx detection cell.

3. The NOx sensor according to claim 2, wherein said oxygen supplying pumping cell for supplying oxygen to at least said first gas treatment chamber is arranged in a second gas treatment chamber communicating with said first gas treatment chamber and said gas detection chamber.

4. The NOx sensor according to claim 2, wherein an anode electrode of said oxygen supplying pumping cell is an oxidation catalyst electrode active to the gas to be treated and oxygen.

5. The NOx sensor according to claim 2, wherein a cathode electrode of said oxygen supplying pumping cell pumping is installed in a duct communicating with the gas to be detected.

6. The NOx sensor according to claim 5, further comprising means for measuring a potential difference between said cathode electrode of said oxygen supplying pumping cell exposed to the gas to be detected and said reference electrode of said NOx detection cell or said counter electrode of said NOx conversion pumping cell communicating with an atmospheric air.

7. The NOx sensor according to claim 1, wherein said first gas treatment chamber is formed in a separate layer from said zirconia solid electrolyte substrates surrounding said gas detection chamber, or surrounding said gas detection chamber and a second gas treatment chamber, and communicates with said gas detection chamber or said second gas treatment chamber through a gas diffusion hole or a porous member arranged in said zirconia solid electrolyte substrate.

8. The NOx sensor according to claim 1, wherein said porous member loaded into said first gas treatment chamber comprises chiefly at least one selected from the group consisting of zeolite, zirconia, alumina, and silica, and a compound thereof.

9. The NOx sensor according to claim 1, wherein said porous member loaded into said first gas treatment chamber carries catalytic oxide and/or precious metal.

10. The NOx sensor according to claim 9, wherein said catalytic oxide comprises ceria or a solid solution of ceria and zirconia.

11. The NOx sensor according to claim 9, wherein said catalytic precious metal carried by said porous member loaded into said first gas treatment chamber comprises one selected from the group consisting of Pt, Pd, Ir, Au, Ru, Ag, Rh, and a mixture thereof.

12. The NOx sensor according to claim 9, wherein the amount of said catalytic precious metal by said porous member loaded into said first gas treatment chamber falls within the range of 0.1 and 30 mg/cm3 with respect to a bulk volume of said porous member.

13. The NOx sensor according to claim 1, further comprising:
   an oxidation catalyst pumping cell including an oxidation catalyst electrode composed of said inorganic porous member loaded into said first gas treatment chamber, said oxidation catalyst electrode comprising an oxygen-ion conductive solid electrolyte and serving as an anode electrode, and a cathode electrode to be paired with said oxidation catalyst electrode, said cathode electrode being arranged on a zirconia solid electrolyte substrate outside said gas detection chamber and being active to oxygen; and
   voltage applying means for applying a predetermined voltage to said oxidation catalyst pumping cell.

14. The NOx sensor according to claim 13, wherein said oxidation catalyst electrode comprises mainly an oxygen-ion-conductive solid electrolyte and a precious metal selected from the group consisting of Pt, Pd, Ir, Au, Rh, a mixture thereof, and an alloy thereof.

15. The NOx sensor according to claim 14, wherein said oxygen-ion-conductive solid electrolyte to be added to said oxidation catalyst electrode falls within the range of 20 and 50% by volume with respect to the volume of said oxidation catalyst electrode.

16. The NOx sensor according to claim 13, wherein said oxidation catalyst electrode comprises chiefly an oxygen-ion-conductive solid electrolyte and a metal oxide active to said reducing gas.

17. The NOx sensor according to claim 13, wherein at least one gas inlet is formed in the top or bottom of said first gas treatment chamber.

18. The NOx sensor according to claim 1, wherein said reference electrode of said NOx sensing cell is installed in said gas detection chamber.

19. The NOx sensor according to claim 1, comprising:
   said reference electrode of said NOx sensing cell being installed across said first zirconia solid electrolyte substrate constituting said gas detection chamber, in a duct leading only to the air outside of said gas detection chamber;

an oxygen sensing electrode arranged in said detection chamber, said oxygen sensing electrode being active to oxygen alone; and means for detecting the total NOx concentration while correcting the same for a potential difference between said reference electrode and said NOx sensing electrode and a potential difference between said reference electrode and said oxygen sensing electrode.

20. The NOx sensor according to claim 1, wherein said gas inlet arranged in said first gas treatment chamber is covered with a porous protective film.

21. A NOx sensor comprising:
a gas detection chamber composed of an internal space formed by a first zirconia solid electrolyte substrate having oxygen ion conductivity, an opposed second zirconia solid electrolyte having oxygen ion conductivity, and a spacer separating said zirconia solid electrolyte substrates;
a NOx detection cell including a NOx sensing electrode fixed onto one side of said first zirconia solid electrolyte substrate in said gas detection chamber, said NOx sensing electrode being active to NOX and oxygen, and a reference electrode fixed onto the other side of said first zirconia solid electrolyte substrate, said reference electrode being active to at least oxygen;
a NOx conversion pumping cell including a NOx conversion electrode fixed onto said second zirconia solid electrolyte substrate in said gas detection chamber, said NOx conversion electrode being active to NOx and oxygen, and a counter electrode to be paired with said NOx conversion electrode, said counter electrode being fixed onto said second zirconia solid electrolyte substrate, being active to oxygen;
voltage applying means for applying a predetermined voltage to said NOx conversion pumping cell;
a first gas treatment chamber communicating with said gas detect ion chamber and having a gas inlet leading to an atmosphere of a gas to be detected;
an oxidation catalyst pumping cell including an oxidation catalyst electrode arranged in said first gas treatment chamber, said oxidation catalyst electrode having a gas channel, being active to a reducing gas and oxygen, and serving as an anode electrode, and a cathode electrode to be paired with said oxidation catalyst electrode, said cathode electrode being arranged on a zirconia solid electrolyte substrate outside said gas detection chamber and being active to oxygen;
voltage applying means for applying a predetermined voltage to said oxidation catalyst pumping cell; and
means for measuring a potential difference between said NOx sensing electrode and said reference electrode NOx when NOx in the gas to be detected is converted into $NO_2$ or NO by said NOx conversion pumping cell after the reducing gas in the gas to be detected is oxidized in said first gas treatment chamber, and thereby detecting the total NOx concentration in the gas to be detected.

22. The NOx sensor according to claim 21, wherein said gas channel arranged in said first treatment chamber is composed of at least one narrow path arranged along the direction of flow of the gas to be detected.

23. The NOx sensor according to claim 22, wherein a diffusion resistance defined by the ratio (S/L) of the total cross-sectional area S of said path to the length L of said path falls within the range of 0.001 and 0.1.

24. A NOx sensor comprising:
a gas detection chamber composed of an internal space formed by a first zirconia solid electrolyte substrate having oxygen ion conductivity, an opposed second zirconia solid electrolyte having oxygen ion conductivity, and a spacer separating said zirconia solid electrolyte substrates;
a NOx sensing cell including a NOx sensing electrode fixed onto one side of said first zirconia solid electrolyte in said gas detection chamber, said NOx sensing electrode being active to NOx and oxygen, and a reference electrode fixed onto the same side of said first zirconia solid electrolyte substrate, said reference electrode being active to oxygen and inactive to NOx;
a NOx conversion pumping cell including a NOx conversion electrode fixed onto said second zirconia solid electrolyte substrate in said gas detection chamber, said NOx conversion electrode being active to NOx and oxygen, and a counter electrode to be paired with said NOx conversion electrode, said counter electrode being fixed onto said second zirconia solid electrolyte substrate, being active to oxygen;
voltage applying means for applying a predetermined voltage to said NOx conversion pumping cell;
a first gas treatment chamber disposed between said gas detection chamber and a gas inlet leading to an atmosphere of a gas to be detected;
an inorganic porous member with a porosity of 5–40% by volume being loaded into only said first gas treatment chamber; and
means for measuring a potential difference between said NOx sensing electrode and said reference electrode while converting NOx in the gas to be detected into single component after a reducing gas in the gas to be detected is oxidized in said first gas treatment chamber, and thereby detecting a total NOx concentration in the gas to be detected.

25. A NOx sensor comprising:
a gas detection chamber composed of an internal space formed by a first zirconia solid electrolyte substrate having oxygen ion conductivity, an opposed second zirconia solid electrolyte having oxygen ion conductivity, and a spacer separating said zirconia solid electrolyte substrates;
a NOx detection cell including a NOx sensing electrode fixed onto one side of said first zirconia solid electrolyte substrate in said gas detection chamber, said NOx sensing electrode being active to NOx and oxygen, and a reference electrode fixed onto the same side of said first zirconia solid electrolyte substrate, said reference electrode being active oxygen and inactive to NOx;
a NOx conversion pumping cell including a NOx conversion electrode fixed onto said second zirconia solid electrolyte substrate in said gas detection chamber, said NOx conversion electrode being active to NOx and oxygen, and a counter electrode to be paired with said NOx conversion electrode, said counter electrode being fixed onto said second zirconia solid electrolyte substrate, being active to oxygen;
voltage applying means for applying a predetermined voltage to said NOx conversion pumping cell;
a first gas treatment chamber communicating with said gas detection chamber and having a gas inlet leading to an atmosphere of a gas to be detected;
an oxidation catalyst pumping cell including an oxidation catalyst electrode arranged in said first gas treatment chamber, said oxidation catalyst electrode having a gas channel, being active to a reducing gas and oxygen, and serving as an anode electrode, and a cathode electrode to be paired with said oxidation catalyst electrode, said cathode electrode being arranged on a zirconia solid electrolyte substrate outside said gas detection chamber and being active to oxygen;

voltage applying means for applying a predetermined voltage to said oxidation catalyst pumping cell; and means for measuring a potential difference between said NOx sensing electrode and said reference electrode while converting NOx in the gas to be detected into $NO_2$ or NO by said NOx conversion pumping cell after the reducing gas in the gas to be detected is oxidized in said first gas treatment chamber, and thereby detecting the total NOx concentration in the gas to be detected.

* * * * *